US008897879B2

(12) United States Patent
Karamanoglu et al.

(10) Patent No.: US 8,897,879 B2
(45) Date of Patent: Nov. 25, 2014

(54) METHOD AND APPARATUS FOR THERAPIES OF THE CARDIOVASCULAR AND CARDIORENAL SYSTEM

(71) Applicant: Medtronic, Inc., Minneapolis, MN (US)

(72) Inventors: Mustafa Karamanoglu, Fridley, MN (US); Vincent E Splett, Apple Valley, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 13/667,925

(22) Filed: Nov. 2, 2012

(65) Prior Publication Data

US 2013/0116743 A1    May 9, 2013

Related U.S. Application Data

(60) Provisional application No. 61/555,939, filed on Nov. 4, 2011.

(51) Int. Cl.
*A61N 1/362* (2006.01)
*A61N 1/36* (2006.01)
*A61N 1/39* (2006.01)
*A61N 1/372* (2006.01)

(52) U.S. Cl.
CPC .......... *A61N 1/3611* (2013.01); *A61N 1/36135* (2013.01); *A61N 1/36142* (2013.01); *A61N 1/36153* (2013.01); *A61N 1/36157* (2013.01); *A61N 1/36171* (2013.01); *A61N 1/36175* (2013.01); *A61N 1/362* (2013.01); *A61N 1/3962* (2013.01); *A61N 1/36017* (2013.01); *A61N 1/37241* (2013.01)
USPC ........................................... 607/42; 607/123

(58) Field of Classification Search
CPC ..... A61N 1/3601; A61N 1/056; A61N 1/0563; A61B 5/4818
USPC ..................................................... 607/42, 123
See application file for complete search history.

(56) References Cited

U.S. PATENT DOCUMENTS

| 4,497,326 | A | 2/1985 | Curry |
| 4,519,973 | A | 5/1985 | Cahalan et al. |
| 4,901,725 | A | 2/1990 | Nappholz et al. |
| 5,117,824 | A | 6/1992 | Keimel et al. |
| 5,265,604 | A | 11/1993 | Vince |
| 5,443,492 | A | 8/1995 | Stokes et al. |
| 5,628,778 | A | 5/1997 | Kruse et al. |
| 5,824,029 | A | 10/1998 | Weijand et al. |
| 5,922,014 | A | 7/1999 | Warman et al. |
| 6,076,015 | A | 6/2000 | Hartley et al. |
| 6,198,952 | B1 | 3/2001 | Miesel |
| 6,666,821 | B2 | 12/2003 | Keimel |
| 6,968,237 | B2 | 11/2005 | Doan et al. |
| 7,031,777 | B2 | 4/2006 | Hine et al. |

(Continued)

OTHER PUBLICATIONS

U.S. Appl. No. 11/810,941, filed Jun. 7, 2007.

*Primary Examiner* — Christopher D Koharski
*Assistant Examiner* — Michael Carey
(74) *Attorney, Agent, or Firm* — Carol F. Barry

(57) ABSTRACT

A system and method for controlling respiration depth or respiration rate is provided. A bipolar pair of a plurality of electrodes is selected in a location for stimulating a phrenic nerve. Electrical stimulation is delivered through a medical electrical lead electrode proximate phrenic nerve tissue. Modulating respiration is elicited in response to electrical stimulation of the phrenic nerve.

41 Claims, 10 Drawing Sheets

(56) References Cited

U.S. PATENT DOCUMENTS

| | | |
|---|---|---|
| 7,363,085 B1 | 4/2008 | Benser et al. |
| 7,831,303 B2 | 11/2010 | Rueter et al. |
| 7,860,580 B2 | 12/2010 | Falk et al. |
| 7,979,128 B2 | 7/2011 | Tehrani et al. |
| 2006/0149334 A1* | 7/2006 | Tehrani et al. ............ 607/42 |
| 2007/0138027 A1 | 6/2007 | Dinsmoor et al. |
| 2009/0036947 A1 | 2/2009 | Westlund et al. |
| 2009/0270729 A1 | 10/2009 | Corbucci et al. |
| 2009/0308395 A1* | 12/2009 | Lee et al. ............ 128/204.23 |

* cited by examiner

METHOD AND APPARATUS FOR
THERAPIES OF THE CARDIOVASCULAR
AND CARDIORENAL SYSTEM

CROSS-REFERENCE TO RELATED
APPLICATION

This application claims the benefit of U.S. Provisional Application No. 61/555,939 filed on Nov. 4, 2011. The disclosure of the above application is incorporated herein by reference in its entirety.

TECHNICAL FIELD

The disclosure relates generally to implantable medical devices and, more particularly, to a method and apparatus for transvenously inducing respiration.

BACKGROUND

Electrical stimulation of the right and left phrenic nerve has been used for treating respiratory insufficiency, e.g. in paralysis, apnea, or other respiratory conditions as recognized by Creasy et al. Electrical Stimulation To Restore Respiration, Journal of Rehabilitation Research and Development, Vol. 33 No. 2, April 1996, pp 123-132. For example, U.S. Pat. No. 7,979,128 to Tehrani et al. (hereinafter Tehrani et al.) asserts that phrenic nerve stimulation can gradually control breathing in order to treat obstructive sleep apnea. Tehrani et al., discloses in claim 1 that electrical stimulation is delivered when an obstructive respiratory event is detected. Electrical stimulation is applied during a first selected intrinsic inspiration cycle at a first delay from an onset of the first intrinsic inspiration cycle. Electrical stimulation is then applied during a second intrinsic inspiration cycle at a second delay from an onset of the second intrinsic cycle. Electrical stimulation is again applied during one or more subsequent intrinsic breaths such that each stimulation is applied with a delay from an onset of each subsequent intrinsic breath such that the delay in each subsequent breath reduces from a previous delay until the stimulation is synchronous with a start of each subsequent intrinsic inspiration wherein the electrical stimulation is provided to tissue associated with the diaphragm of the patient at least in part during the intrinsic inspiration cycle in accordance with the electrical stimulation protocol until the sensed respiration has reached a normalized respiration such that ventilatory stability is improved. Variable delay to deliver stimulation to the phrenic nerve is used to achieve a synchronous normalized breathing pattern and does not provide a more robust breathing pattern U.S. Pat. No. 5,265,604 to Vince discloses innervating one of both denervated diaphragms of a patient synchronously. Muscle contraction is detected through a sensor near the pharyngeal muscle within the pharynx at the onset of inspiration and the intensity of the muscle contraction, and produces a signal representative of rate and intensity of pharyngeal muscle contraction at onset of inspiration.

U.S. Pat. No. 7,363,085 to Benser et al. discloses that phrenic nerve stimulation is used to avoid Cheyne Stokes Syndrome (CSS) that typically occurs during sleep. CSS involves tidal volume of the lungs oscillating between hyperpnea and hypopnea or apnea with a periodicity 70 seconds. Benser et al. senses respiratory data from the patient. When the respiratory data indicates that the upper airway may collapse, electrical stimulation is delivered to the phrenic nerve in order to prevent the upper airway from collapsing.

A need remains for an implantable medical device to automatically deliver electrical stimulation to the right or left phrenic nerve through stimulation methods and associated apparatus for effectively delivering phrenic nerve stimulation for respiration therapies.

DETAILED DESCRIPTION

In the following description, references are made to illustrative embodiments. It is understood that other embodiments may be utilized without departing from the scope of the disclosure.

Figure 1:
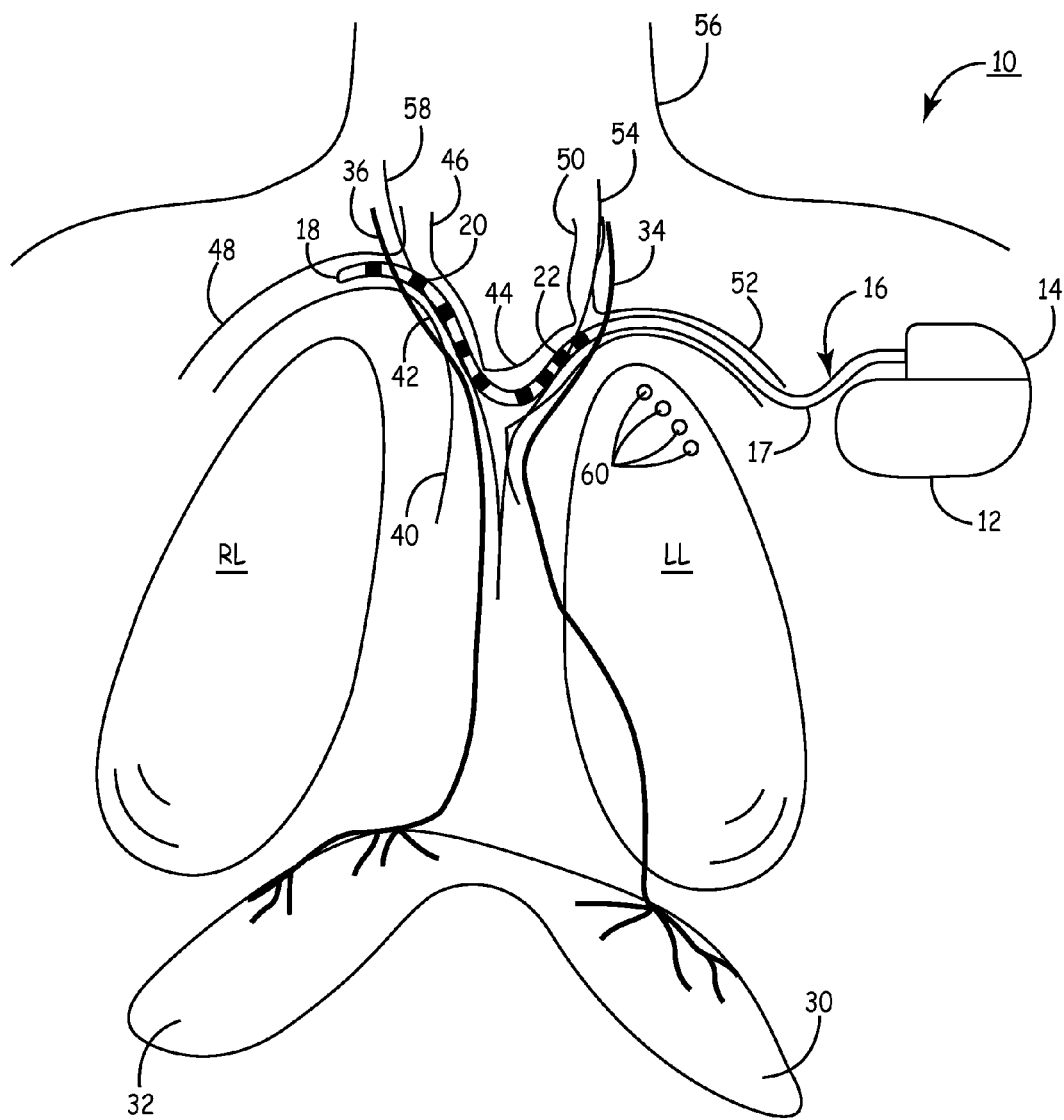
FIG. 1 is a schematic view of an implantable medical device (IMD) system for delivering phrenic nerve stimulation according to one embodiment.

FIG. 1 is a schematic view of an implantable medical device (IMD) system for delivering phrenic nerve stimulation. IMD 10 includes a housing 12 enclosing electronic circuitry (not shown) included in IMD 10 and a connector block 14 having a connector bore for receiving at least one medical electrical lead 16 and providing electrical connection between electrodes carried by lead 16 and IMD internal electronic circuitry. IMD 10 includes devices such as neurostimulators and/or a combination cardio-neurostimulators. An example of a neurostimulator may be seen with respect to U.S. patent application Ser. No. 11/810,941 filed on Jun. 7, 2007, now U.S. Pat. No. 8,666,506, issued Mar. 4, 2014 and assigned to the assignee of the present invention, the disclosure of which is incorporated by reference in its entirety herein.

In FIG. 1, the left phrenic nerve 34 and the right phrenic nerve 36 are shown innervating the respective left diaphragm 30 and right diaphragm 32. The anatomical locations of the left phrenic nerve 34, the right phrenic nerve 36 and other anatomical structures shown schematically in the drawings presented herein are intended to be illustrative of the approximate and relative locations of such structures. These structures are not necessarily shown in exact anatomical scale or location. Left phrenic nerve 34 is shown schematically to extend in close proximity to the left internal jugular vein (LJV) 50, the left subclavian vein (LSV) 52, and the left innominate vein (LIV) 44, also referred to as the left brachiocephalic vein.

The anatomical location of the right phrenic nerve 36 is shown schematically to extend in close proximity to the right internal jugular vein (RJV) 46, the right subclavian vein (RSV) 48, the right innominate vein (RIV) 42 (also referred to as the right brachiocephalic vein), and the superior vena cava (SVC) 40.

The anatomical location of the vagus nerve 54 and 58 is schematically shown as extending from the neck 56 and thorax to the abdomen. The left vagus nerve 54 crosses in front of the left subclavian artery to enter the thorax between the left common carotid and subclavian arteries. The left vagus nerve 54 descends on the left side of the aortic arch, which separates it from the left pleura, and travels behind the phrenic nerve. The left vagus nerve 54 courses behind the root of the left lung and then deviates medially and downwards to reach the esophagus and form the esophageal plexus by joining the opposite (right) vagus nerve 58.

Stretch receptors 60, mechanoreceptors responsive to distention of various organs and muscles, are neurologically linked to the medulla in the brain stem via afferent nerve fibers. Exemplary stretch receptors can be located in the heart, the great veins, and the lungs. Respiration affects stretch receptors 60, which, in turn, affects vagal and sympathetic nervous system in the brain. Through modulation of the respiration, the amplitude from the stretch receptors effect could be controlled.

Lead 16 is a multipolar lead carrying proximal electrodes 22 spaced proximally from distal electrodes 20, positioned at or near the distal end 18 of lead 16. Skilled artisans appreciate that other embodiments can rely on any one of the medical electrical leads described or incorporated herein. In one or more embodiments, at least one proximal bipolar pair of electrodes is provided for stimulating the left phrenic nerve 34 and at least one distal bipolar pair of electrodes is provide for stimulating the right phrenic nerve 36. In various embodiments, two or more electrodes may be spaced apart along the lead body, near the distal tip 18 of lead 16, from which at least one pair of electrodes is selected for delivering stimulation to the right phrenic nerve 36. Additionally, two or more electrodes may be positioned along spaced apart locations proximally from the distal electrodes 20 from which at least one pair of electrodes is selected for delivering stimulation to the left phrenic nerve 34.

Lead 16 includes an elongated lead body 17, which may have a diameter in the range of approximately 2 French to 8 French, and typically approximately 4 French to approximately 6 French. The lead body carries the electrodes 20 and 22 which are electrically coupled to electrically insulated conductors extending from respective individual electrodes 20 and 22 to a proximal connector assembly adapted for connection to IMD connector block 14. Lead 16 may be provided with a fixation element for fixing the position of the lead once a desired implant location is identified. Exemplary leads that can be useful for the present disclosure include U.S. Pat. Nos. 5,922,014, 5,628,778, 4,497,326, 5,443,492, 7,860, 580 filed Apr. 30, 2008 such that electrodes are added and/or spaced apart in a manner similar to that disclosed in the figures of the present application, all of listed patents and applications are incorporated by reference in their entirety. Additional lead and electrode configurations that may be adapted for use with the present disclosure by adjusting lead shape, length, electrode number and/or electrode to effectively provide phrenic nerve stimulation as described herein are generally disclosed in U.S. Pat. Nos. 7,031,777, 6,968, 237, and US Publication No. 2009/0270729, filed Apr. 25, 2008, all of which are incorporated herein by reference in their entirety.

In one embodiment, distal tip 18 of lead 16 is advanced to a location along the RIV 42 and further along the RSV 48 or the RJV 46 to position distal electrodes 20 in operative relation to right phrenic nerve 36 for delivering stimulation pulses to nerve 36 to activate the right diaphragm 32. The proximal electrodes 22 may be appropriately spaced from distal electrodes 20 such that proximal electrodes 22 are positioned along the LIV 44 and/or along the junction of the LSV 52 and LJV 50 for delivering stimulation pulses to the left phrenic nerve 34 to activate the left diaphragm 30.

In various embodiments, lead 16 may carry four or more electrodes spaced at selected distances to provide at least one pair near a distal lead tip 18 for right phrenic nerve stimulation and at least one pair more proximally for left phrenic nerve stimulation. In other embodiments, lead 16 may carry multiple electrodes spaced equally along a portion of the body of lead 16 such that any pair may be selected for right phrenic nerve stimulation and any pair may be selected for left phrenic nerve stimulation based on the relative locations of the electrodes from the nerves. Furthermore, it is recognized that in some embodiments, stimulation of only one of the right or left phrenic nerve may be required and an appropriate number and location of electrodes may be provided along lead 16 for such purposes.

Figure 2:
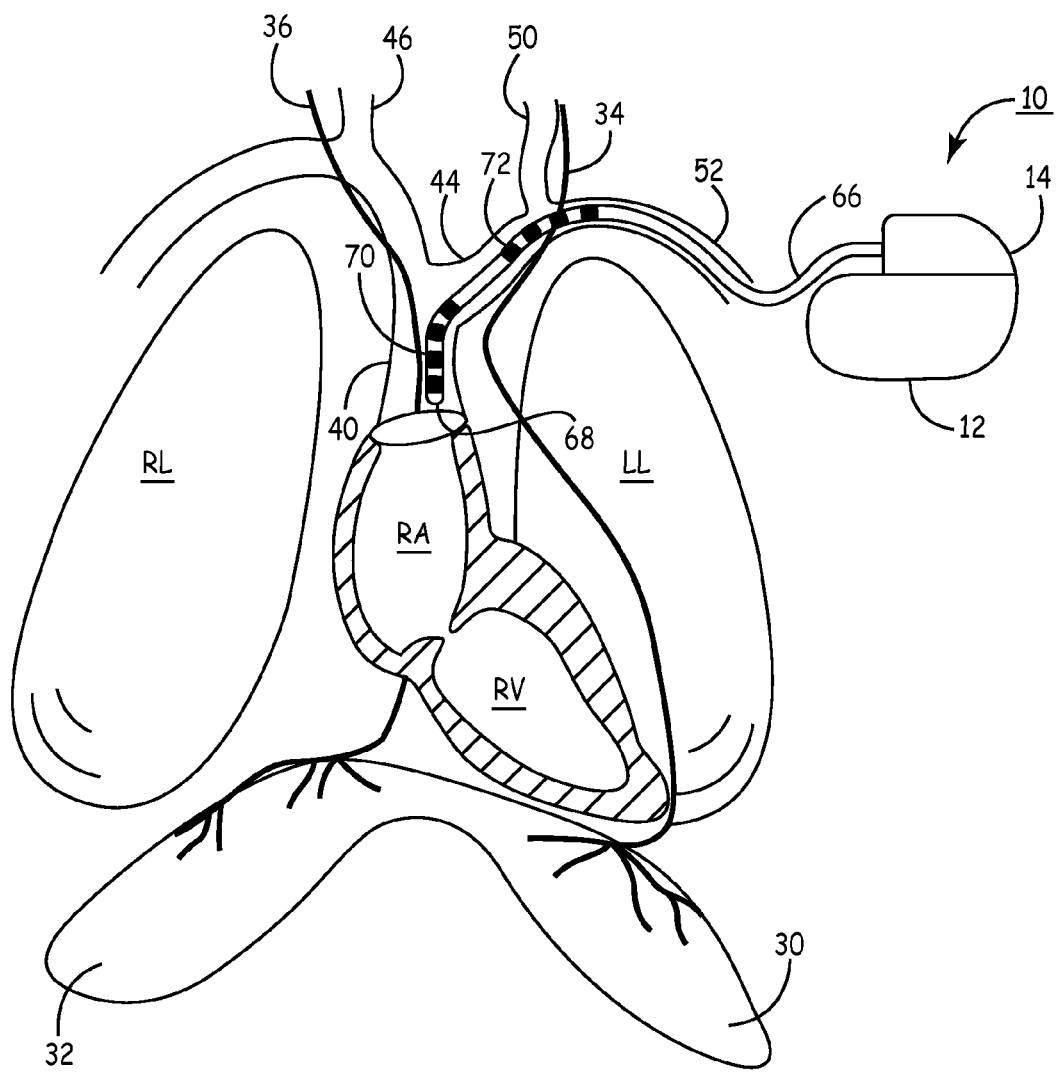
FIG. 2 is a schematic view of an IMD system for delivering phrenic nerve stimulation according to an alternative embodiment.

FIG. 2 is a schematic view of an IMD system for delivering phrenic nerve stimulation according to an alternative embodiment. In FIG. 2, the right atrium (RA) and the right ventricle (RV) are shown schematically in a partially cut-away view. The right phrenic nerve 36 extends posteriorly along the SVC 40, the RA and the inferior vena cava (IVC) (not shown in FIG. 2). The left phrenic nerve 34 normally extends along a left lateral wall of the left ventricle (not shown). The SVC 40 enters the RA. A lead 66 is coupled to IMD 10 via connector block 14. Lead 66 carries multiple electrodes, which may be spaced apart into a plurality of distal electrodes 70 located near distal lead tip 68 and a plurality of proximal electrodes 72. The distal tip 68 of lead 66 is advanced into SVC 40 to position distal electrodes 70 for stimulating the right phrenic nerve 36. The proximal electrodes 72 are used to stimulate the left phrenic nerve 34, e.g. along the LIV 44 or junction of the LJV 50 and LSV 52.

Figure 3:
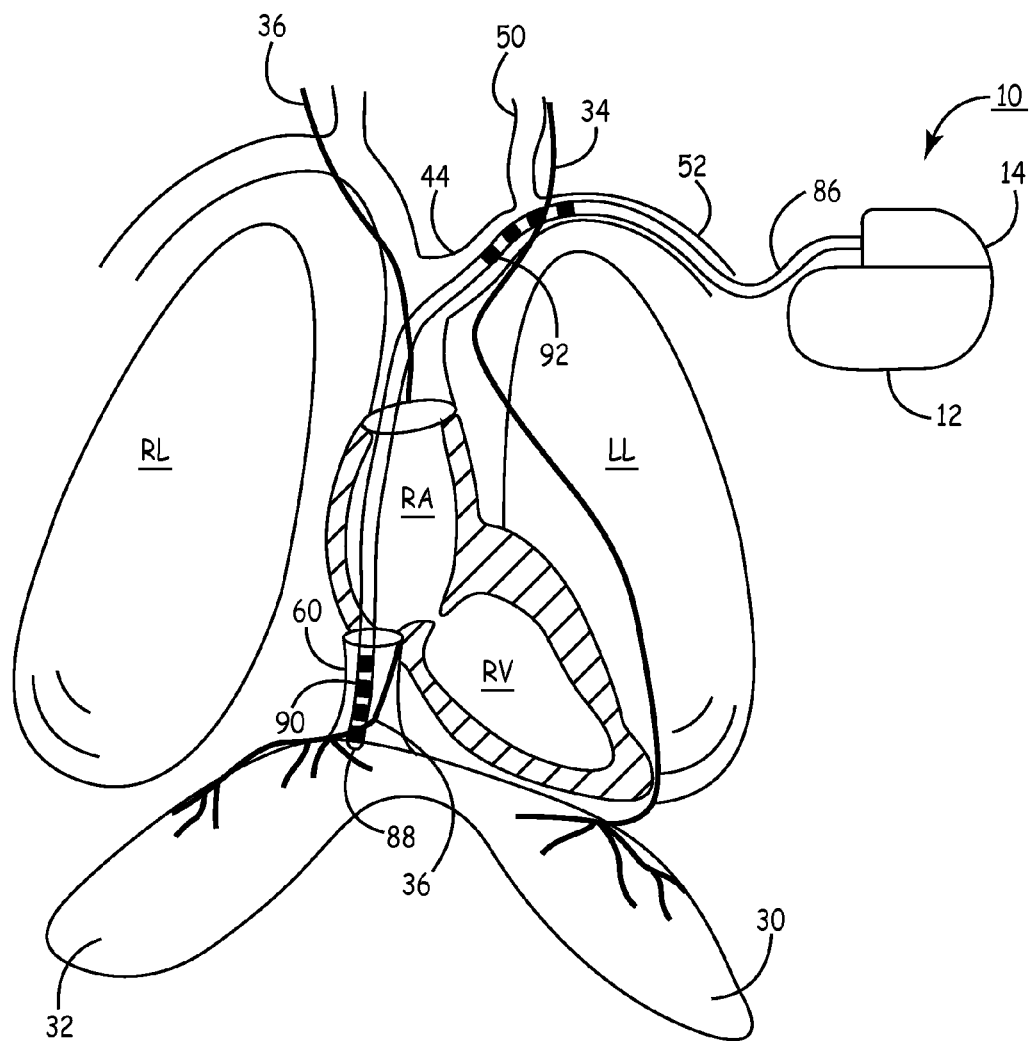
FIG. 3 is a schematic view of an IMD system for delivering phrenic nerve stimulation according to another alternative embodiment.

FIG. 3 is a schematic view of an IMD system for delivering phrenic nerve stimulation according to another alternative embodiment. In FIG. 3, the inferior vena cava (IVC) 60, which empties into the RA, is shown schematically. In this embodiment, lead 86 extends from IMD connector block 14 to the IVC 60 to position electrodes 90, carried by lead 86 at or near distal lead tip 88, along the IVC 60 adjacent the right phrenic nerve 36 near the level of the diaphragm, e.g. approximately at the height of the eighth thoracic vertebra (T8) (not shown). Proximal electrodes 92 are positioned proximally along lead 86 for positioning along the LIV 44 or junction of the LJV 50 and LSV 52 for providing stimulation to the left phrenic nerve 34.

Electrodes used for stimulating the right phrenic nerve and electrodes used for stimulating the left phrenic nerve are shown configured along a common lead in FIGS. 1 through 3. In alternative embodiments it is contemplated that two leads, one for stimulating the left and one for stimulating the right phrenic nerve, may be provided separately. Whether provided as a single lead or two leads, either lead placed along the venous locations shown may become dislodged into the right atrium or located near enough to the heart to cause inadvertent capture of the cardiac tissue directly or nerves that innervate cardiac tissue, such as the vagus nerve or other sympathetic nerves. Methods described herein provide an implant and therapy delivery technique to minimize the risk of inadvertent cardiac stimulation, or cardiac nerve stimulation, during a phrenic nerve stimulation therapy.

The housing 12 of IMD 10 may be provided as an indifferent electrode for use in combination with any of the lead-based electrodes shown in FIGS. 1 through 3 for some monitoring purposes. As will be further described below, the electrodes included in an IMD system for delivering a phrenic nerve stimulation therapy may additionally be used for sensing cardiac electrical signals (EGM) signals and for measuring thoracic impedance signals. In some embodiments, the housing 12 may provide an indifferent electrode for sensing EGM signals, delivering a drive current during thoracic impedance measurements or used in a measurement pair for monitoring thoracic impedance.

It is further recognized that additional leads and electrodes may be included in an IMD system capable of delivering transvenous phrenic nerve stimulation (tvPNS). For example, IMD 10 may be coupled to cardiac leads, which may be subcutaneous leads, transvenous leads positioned in or along a heart chamber, or epicardial leads. IMD 10 may incorporate sensing electrodes along housing 12. IMD 10 may be provided specifically for delivering phrenic nerve stimulation (with associated monitoring of sensed signals for controlling the phrenic nerve stimulation) or may include other therapy delivery capabilities such as cardiac pacing (e.g. for bradycardia pacing, cardiac resynchronization therapy, or anti-tachycardia pacing) cardioversion/defibrillation shocks, drug delivery or the like. As such, the IMD system may include other leads, electrodes and/or catheters not shown in FIGS. 1 through 3 as needed for other IMD functions. In some embodiments, electrodes used for delivering phrenic nerve stimulation could be carried by leads that additionally carry cardiac pacing, sensing and/or defibrillation electrodes. In other embodiments, sensing electrodes carried by cardiac leads may be used for sensing EGM signals to detect inadvertent cardiac capture or cardiac nerve stimulation for use in controlling a phrenic nerve stimulation therapy and during positioning of the phrenic nerve stimulation electrodes.

In FIGS. 1 through 3, IMD 10 is shown in a left pectoral position such that it is the distal electrodes, e.g., electrodes 20, 70, or 90 that are positioned in operative relation to the right phrenic nerve 36 and the proximal electrodes, e.g., electrodes 22, 72, or 92, that are positioned in operative relation to the left phrenic nerve 34. Depending on the implanted configuration, a phrenic nerve stimulation lead, e.g. lead 16 or 66, may be positioned entering a vein from a right venous approach such that it is the distal electrodes 20 or 70, that are positioned for left phrenic nerve stimulation and the proximal electrodes 22 or 72 that are positioned for right phrenic nerve stimulation. For example, IMD 10 may be implanted in a pocket along a right pectoral position, along a right or left abdominal position, centrally, or other implant location. The IMD implant location may determine whether it is the proximal electrodes or the distal electrodes that are positioned for stimulating the right or the left phrenic nerves, when the electrodes are all carried by a single phrenic nerve stimulation lead.

For example, a right-sided implantation of IMD 10 could include distal electrodes positioned along the LIV 44 for left phrenic nerve stimulation and proximal electrodes positioned for right phrenic nerve stimulation along the RIV 42 or junction of the RSV 48 and RJV 46. As such, in the methods described hereafter, testing and monitoring for EGM sensing, cardiac capture, and/or non-phrenic nerve capture may involve testing of proximal and/or distal electrodes depending on the particular implant configuration being used.

Figure 4:
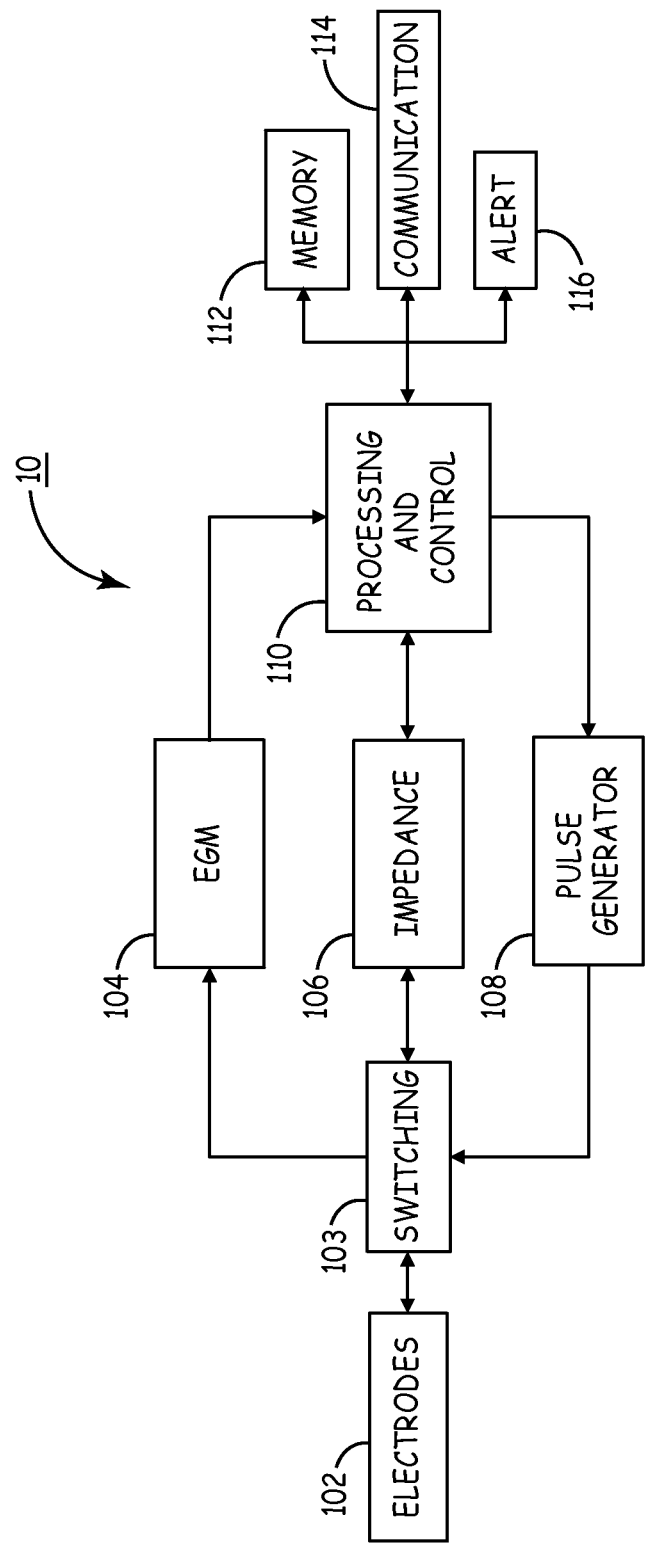
FIG. 4 is a functional block diagram of an IMD that may be associated with any of the leads and implant locations shown in FIGS. 1 through 3.

FIG. 4 is a functional block diagram of an IMD that may include any of the leads and implant locations shown in FIGS. 1 through 3. Electrodes 102 are coupled to EGM sensing 104, impedance sensing 106, and pulse generator 108 via switching circuitry 103. Electrodes 102 may correspond to any of the electrodes shown in FIGS. 1 through 3 or other electrodes carried along one or more leads for delivering phrenic nerve stimulation. Electrodes 102 may further include other electrodes available along the IMD housing and any other subcutaneous or cardiac leads coupled to IMD 10.

Electrodes 102 are selected via switching circuitry 103 for coupling to EGM sensing circuitry 104 to sense for the presence of EGM signals on phrenic nerve stimulation electrodes and/or for evidence of inadvertent capture of the heart or cardiac nerves. Electrodes 102 may also be selected in impedance signal drive current and measurement pairs via switching circuitry 103 for monitoring thoracic impedance by impedance monitoring circuitry 106. Electrodes 102 are further selected via switching circuitry 103 for delivering phrenic nerve stimulation pulses generated by pulse generator 108.

EGM sensing circuitry 104 is provided for sensing for the presence of an EGM signal on phrenic nerve stimulation electrodes during implantation and during nerve stimulation therapy delivery for detecting a potential risk for cardiac capture. If the electrodes selected for phrenic nerve stimulation are located in close proximity of the heart, nerve stimulation pulses may inadvertently be delivered to the heart, potentially capturing myocardial tissue and inducing arrhythmias. If an EGM signal can be sensed using the electrodes selected for phrenic nerve stimulation, the electrodes may be too close or within the heart. As such, determining that an EGM signal can be sensed using phrenic nerve stimulation electrodes indicates a risk of unintentional cardiac stimulation.

Additionally or alternatively, EGM sensing circuitry 104 is provided for sensing cardiac signals for detecting capture of the heart or a cardiac nerve (e.g. vagus nerve or other sympathetic nerves which may affect heart rate) during phrenic nerve stimulation. In this case, the EGM sensing circuitry may be coupled to any of the phrenic nerve lead electrodes, cardiac electrodes, or subcutaneous electrodes positioned for sensing cardiac EGM or ECG signals such that cardiac events (P-waves or R-waves) may be sensed and used to determine if phrenic nerve stimulation is affecting the rate of these sensed cardiac events.

The impedance sensing circuitry 106 includes drive current circuitry and impedance measurement circuitry for monitoring thoracic impedance. The thoracic impedance measurements can be used to select optimal electrodes and stimulation parameters for achieving a desired effect on respiration caused by phrenic nerve stimulation. Respiration can be considered the transport of oxygen from the atmosphere to cells within tissues and the transport of carbon dioxide in the opposite direction. Ventilation, a component of respiration, comprises moving ambient air into and out of the alveoli of the lungs. Ventilation is inspiration and expiration.

It is recognized that other types of physiological sensors, such as pressure sensors, EMG electrodes or accelerometers may be used for sensing a respiratory response to phrenic nerve stimulation and may be substituted or used in addition to thoracic impedance monitoring. Additionally, oxygen sensors and/or chemical sensors can also be employed such as that which is seen with respect to U.S. Pat. No. 6,198,952 issued Mar. 6, 2001, U.S. Pat. No. 6,666,821 issued Dec. 23, 2003 and assigned to the assignee of the present invention, the disclosure of which is incorporated by reference in its entirety herein.

Processing and control 110 receives signals from EGM sensing 104 and impedance sensing circuitry 106. In response to received signals processing and control 110 controls delivery of phrenic nerve stimulation by pulse generator 108. Processing and control 110 may be embodied as a programmable microprocessor and associated memory 112. Received signals may additionally include user command signals received by communication circuitry 114 from an external programming device and used to program processing and control 110. Processing and control 110 may be implemented as any combination of an application specific integrated circuit (ASIC), an electronic circuit, a processor (shared, dedicated, or group) and memory that execute one or more software or firmware programs, a combinational logic circuit, or other suitable components that provide the described functionality.

Memory 112 stores data associated with the monitored EGM (or ECG) and impedance signals. Data may be transmitted to an external device by communication circuit 114, which typically includes wireless transmitting and receiving circuitry and an associated antenna for bidirectional communication with an external device. Processing and control 110 may generate reports or alerts that are transmitted by communication circuitry 114.

Alert circuitry 116 may be provided for generating a patient alert signal to notify the patient or a clinician of a condition warranting medical attention. In one embodiment, an alert is generated in response to sensing an EGM signal using the phrenic nerve stimulation electrodes and/or detecting inadvertent capture of the heart or cardiac nerves. EGM sensing or inadvertent capture of the heart or cardiac nerves indicates possible lead dislodgement and risk of cardiac stimulation that may adversely affect heart rate or induce arrhythmias. The patient may be alerted via an audible sound, perceptible vibration, IMD pocket stimulation, or the like and be advised to seek medical attention upon perceiving an alert signal.

Figure 5:
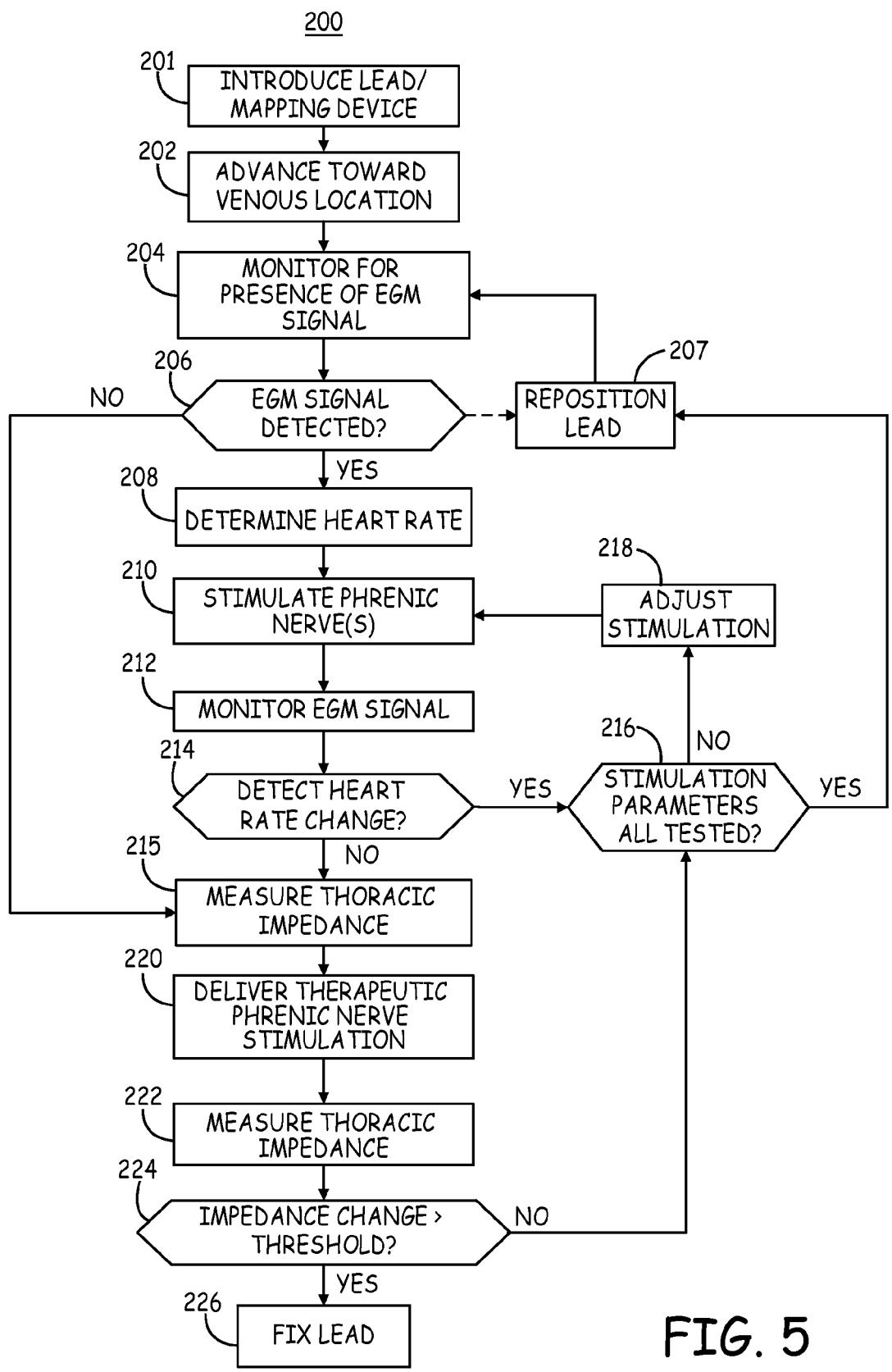
FIG. 5 is a flow chart of a method for positioning a lead for phrenic nerve stimulation according to one embodiment.

Numerous ways exist in which leads can be placed near or directly contact the phrenic nerve. FIG. 5 is a flow chart 200 of a method for delivering electrical stimulation therapy through a medical electrical lead for phrenic nerve stimulation according to one embodiment. At block 201, the phrenic nerve stimulation lead, or a mapping device, is introduced via a venous puncture and vein introducer device. The lead or mapping device is advanced toward a targeted venous location at block 202. Lead or device advancement may be facilitated with the use of fluoroscopy or other imaging method to visualize the location of the lead or mapping device along the venous vasculature.

In one or more embodiments, a mapping device is provided in the form of a guide or delivery catheter that includes electrodes that can be used for sensing physiological signals such as cardiovascular data (e.g. EGM signals) and/or respiratory data The electrodes may additionally be used for delivering stimulation pulses to test phrenic nerve stimulation. The electrodes may be located at positions along the catheter that correspond to electrode locations on a phrenic nerve stimulation lead. Such a mapping device may be considered a "phrenic nerve stimulation lead" because it carries electrodes that can be used for testing phrenic nerve stimulation but is intended for temporary use for mapping and for guiding a chronically implantable phrenic nerve stimulation lead to a desired implant location.

Advancement of a lead toward a venous location may include the use of a guide catheter and/or guide wire. The nerve stimulation lead may be an "over the wire" type lead that includes an open lumen for receiving a guide wire, over which the lead is advanced for placement at a desired venous location. Alternatively, the lead may be sized to be advanced within a lumen of a guide catheter that is then retracted for monitoring signals and testing phrenic nerve stimulation.

Electrodes carried by the phrenic nerve stimulation lead (or mapping device) are coupled to an EGM sense amplifier for observing whether an EGM signal can be sensed by any of the electrodes carried by the lead during its advancement, at block 204. The EGM sense amplifier may be included in EGM sensing circuitry in the IMD. The lead may be coupled directly to the IMD during the implantation procedure with EGM sensing circuitry output transmitted to an external device for display and observation by a clinician. Alternatively, the lead (or mapping device) may be coupled to external test apparatus that includes EGM sensing circuitry and cardiac signal display. The test apparatus and IMD can also be configured to receive and process respiratory data sensed through electrodes on a medical electrical lead. An example of such a configuration may be seen with respect to U.S. Pat. No. 7,831,303 issued Nov. 9, 2010, and assigned to the assignee of the present invention, the disclosure of which is incorporated by reference in its entirety herein.

When the lead carries multiple electrodes, the electrodes may be selected sequentially in bipolar pairs for determining if an EGM signal can be sensed using any bipolar pair carried by the lead. For example, switching circuitry may be provided for selecting which electrodes are being tested. Switching may be performed manually through a user command. The user may then observe a telemetered signal sensed by the selected electrodes to determine if an EGM signal is being sensed.

Alternatively, switching circuitry may be controlled automatically by the IMD or external test device controller to cycle through different electrode combinations. Automatic detection of an EGM signal by the IMD or an external test apparatus may occur upon sensing regularly occurring R-waves or P-waves or identifying an EGM signal morphology. An EGM signal detection alert may then be generated automatically.

Alternatively, the most distal bipolar pair may be monitored as the lead or catheter is advanced since the most distal pair may be the first pair likely to pick up an EGM signal as the lead or catheter is generally advanced from a venous puncture site toward the heart to a desired venous location.

Detection of an EGM signal at block 206 may be based on sensing P-waves or R-waves using a sense amplifier and auto-adjusting threshold, for example as generally described in U.S. Pat. No. 5,117,824 (Keimel, et al.), hereby incorporated herein by reference in its entirety. The rate of sensed events may be compared to an expected range of possible heart rates to indicate regular R-wave or P-wave sensing. Additionally or alternatively, a morphology analysis may be performed at decision block 206 to compare the morphology of an unknown sensed signal to a known EGM signal morphology template to determine if the unknown morphology approximately matches the EGM signal morphology. The displayed signal may be inspected by a user instead of or in addition to an automatic signal analysis for detecting the presence of an EGM signal sensed by the phrenic nerve stimulation electrodes.

In some embodiments, detection of an EGM signal at block 206 may include a signal amplitude criterion. For example, R-wave sensing at or above a predefined sensing threshold or R-wave peak amplitudes exceeding a predefined amplitude may be required before lead repositioning is necessary. Low level signals may indicate that the electrodes are far enough from the heart that cardiac capture is not expected to occur.

A dashed arrow to block 207 indicates the option of repositioning the lead if an EGM signal is sensed. The lead or mapping device may be repositioned at block 207 until no sensing of an EGM signal is present (block 206). If no EGM signal is sensed, the electrodes may be assumed to be far enough from the heart to avoid cardiac capture. In one embodiment, stimulation of the phrenic nerve using the selected bipolar pair at the current implant position is enabled in response to no EGM signal being sensed by a selected pair of electrodes. The process advances directly from block 206 to block 215 to measure thoracic impedance and evaluate a respiratory response to the phrenic nerve stimulation using the selected electrodes.

In addition to or alternatively to monitoring for EGM signal sensing, detection of inadvertent capture of the heart or cardiac nerves may be performed during the implantation procedure. If an EGM signal is sensed at block 206, a pre-stimulation heart rate is optionally determined at block 208 for detecting changes in heart rate due to inadvertent capture of the heart or cardiac nerves.

At block 210, electrical stimulation pulses are delivered to the right, left or both phrenic nerves, individually or synchronously. In some embodiments, a single stimulation pulse is delivered at block 210 at a rate higher than an intrinsic heart rate. The timing of stimulation pulses may be controlled to avoid delivering a stimulation pulse during the cardiac vulnerable period.

The EGM (or an ECG) signal is monitored at block 212. Any available electrodes may be used for monitoring a heart rate signal to detect a change in heart rate due to phrenic nerve stimulation. If the heart rate changes as determined at block 214 when phrenic nerve stimulation is initiated, capture of the heart or cardiac nerves is likely. For example, if the heart rate increases or matches the rate of single stimulation pulses being delivered to the phrenic nerve(s), as determined at block 214, the nerve stimulation pulses are capturing and pacing the heart.

Phrenic nerve stimulation pulses may be delivered at block 210 at a maximum stimulation amplitude and/or pulse width, i.e. a maximum pulse energy, to determine if this high pulse energy causes a heart rate change. If not, it can be assumed that the phrenic nerve(s) can be safely stimulated using the selected electrodes without causing inadvertent cardiac capture or cardiac nerve stimulation.

In other embodiments, the stimulation delivered at block 210 may be a "therapeutic" stimulation pattern of pulse trains delivered at a desired respiration rate to achieve a respiratory response. The heart rate may be monitored to see if these pulse trains cause any unintended effect on heart rate.

If a cardiac nerve is being stimulated above its stimulation threshold, the heart rate may decrease. For example, vagal nerve stimulation causes a decreased heart rate response. As such, detection of a heart rate change determined at block 214 may include detecting an increase or a decrease in heart rate, which may or may not be a rate that matches the phrenic nerve stimulation rate.

If a change in heart rate is detected at block 214 that indicates capture of the heart and/or a cardiac nerve, a stimulation parameter may be adjusted at block 218. Different stimulation parameter settings may be tested until no heart rate change is detected or until a selected number of possible stimulation parameter settings or combinations have been tested (block 216). Stimulation parameters that may be adjusted at block 218 include, but are not limited to, pulse amplitude, pulse number, pulse train frequency, selected stimulation electrodes, and electrode polarity.

If no change in heart rate is detected at block 214, phrenic nerve stimulation may be delivered using the selected electrodes. Before starting a therapeutic level of phrenic nerve stimulation, a thoracic impedance measurement may be made at block 215 to determine a baseline respiration measurement when phrenic nerve stimulation is not being delivered. The thoracic impedance measurement may be made using any available electrodes.

Multiple impedance measurements may be made across different measurement vectors. For example electrodes that provide an impedance measurement substantially across or within the right thoracic cavity may be obtained to assess stimulation of the right phrenic nerve and electrodes that provide an impedance measurement substantially across or within the left thoracic cavity may be obtained to assess stimulation of the left phrenic nerve. Alternatively or additionally to right- and/or left-sided impedance measurements, impedance measurements corresponding to a measurement volume that includes portions of both the right and left thoracic cavity may be obtained. The measurements taken at block 215 are pre-stimulation measurements taken to establish a baseline respiration measurement before phrenic nerve stimulation therapy is initiated.

In the illustrative embodiments, thoracic impedance measurements are described herein for assessing the effectiveness of phrenic nerve stimulation. Other measurements correlated to respiration or diaphragmatic activation may be substituted or used in addition to the thoracic impedance measurements. Other measurements may include, but are not limited to, air flow measurements, diaphragmatic EMG signal measurements, fluoroscopic or other imaging techniques, manual palpation, accelerometer or other motion sensor measurements, and thoracic pressure measurements.

If single pulses or other test parameter settings were used at block 210 to first detect a heart rate change in response to phrenic nerve stimulation, the phrenic nerve stimulation may be adjusted at block 220 to a therapeutic phrenic nerve stimulation pattern. For example, if single pulses were delivered at block 212, the phrenic nerve stimulation may be adjusted to pulse trains delivered at an intended respiratory rate at block 220.

A thoracic impedance measurement is made at block 222 to measure a respiratory response to the phrenic nerve stimulation. The impedance measurement performed at block 215 prior to phrenic nerve stimulation is repeated at block 222 using the same measurement vector(s). The thoracic impedance signal will be a cyclic signal that decreases to a minimum during expiration as the lungs empty and increases to a maximum during inhalation as the lungs fill with air producing a higher thoracic impedance. A thoracic impedance measurement may be an average impedance, a maximum impedance, a maximum to minimum difference (peak-to-peak difference), a slope, an area, or other measurement correlated to respired volume, any of which may be averaged over one or more respiration cycles and taken alone or in any combination.

The pre-stimulation impedance measurement and the impedance measurement obtained during phrenic nerve stimulation therapy are compared at block 224 to determine if a change in the impedance measurement is at least greater than a desired threshold level of improvement. The impedance change may be measured as a difference or ratio of the pre-stimulation impedance measurement and the measurement obtained during stimulation. A threshold change may be a percentage increase over the pre-stimulation measurement. The threshold comparison used at block 224 may be tailored to individual patients and will depend on the particular needs and therapy objectives for a given patient.

If the impedance change is not acceptable at block 224, other stimulation parameters may be tested by adjusting the stimulation at block 218. Stimulation adjustments may include, but are not limited to, pulse amplitude, pulse number, pulse train frequency, selected stimulation electrodes, and electrode polarity.

If all electrode combinations available and a maximum number of stimulation pulse train control parameters (e.g., different settings and combinations of settings for pulse amplitude, pulse frequency, and pulse number) have been tested, as determined at decision block 216, the lead may be repositioned by returning to block 207. If the lead is repositioned, the presence of EGM signal sensing and/or detection of heart rate change due to phrenic nerve stimulation are checked for again by looping back to block 204 or back to block 208. The process of verifying a lead position that does not result in EGM signal sensing and/or cardiac capture or heart rate change and does result in a desired improvement in the impedance measurement (or other measurement correlated to respiration) is repeated.

Once the desired improvement is achieved (block 224), the phrenic nerve stimulation lead is fixed in place at block 226. Lead fixation may involve suturing a proximal portion of the lead or the use of lead fixation members. After lead fixation, the lead may be coupled to the IMD and a phrenic nerve stimulation therapy enabled.

Flow chart 200 presents a lead implantation procedure according to one embodiment. It is recognized that the procedures described in conjunction with flow chart 200 may be performed in a different order than described here or some procedures may be omitted in a method for determining an acceptable location for a phrenic nerve lead and selecting phrenic nerve stimulation electrodes and stimulation parameters. For example, the method may include one or more actions such as sensing for EGM signals present on phrenic nerve lead electrodes, detecting a heart rate change using any available electrodes, and/or sensing respiratory data while determining the optimal location for placing a medical electrical lead. Furthermore, it is contemplated that monitoring of cardiac signals may be performed throughout the processes shown by blocks 220 through 224 when measurements and necessary adjustments are being made to obtain a desired respiratory response in order to determine if phrenic nerve stimulation begins to capture the heart or a cardiac nerve causing a change in heart rate during this process.

Figure 6A:
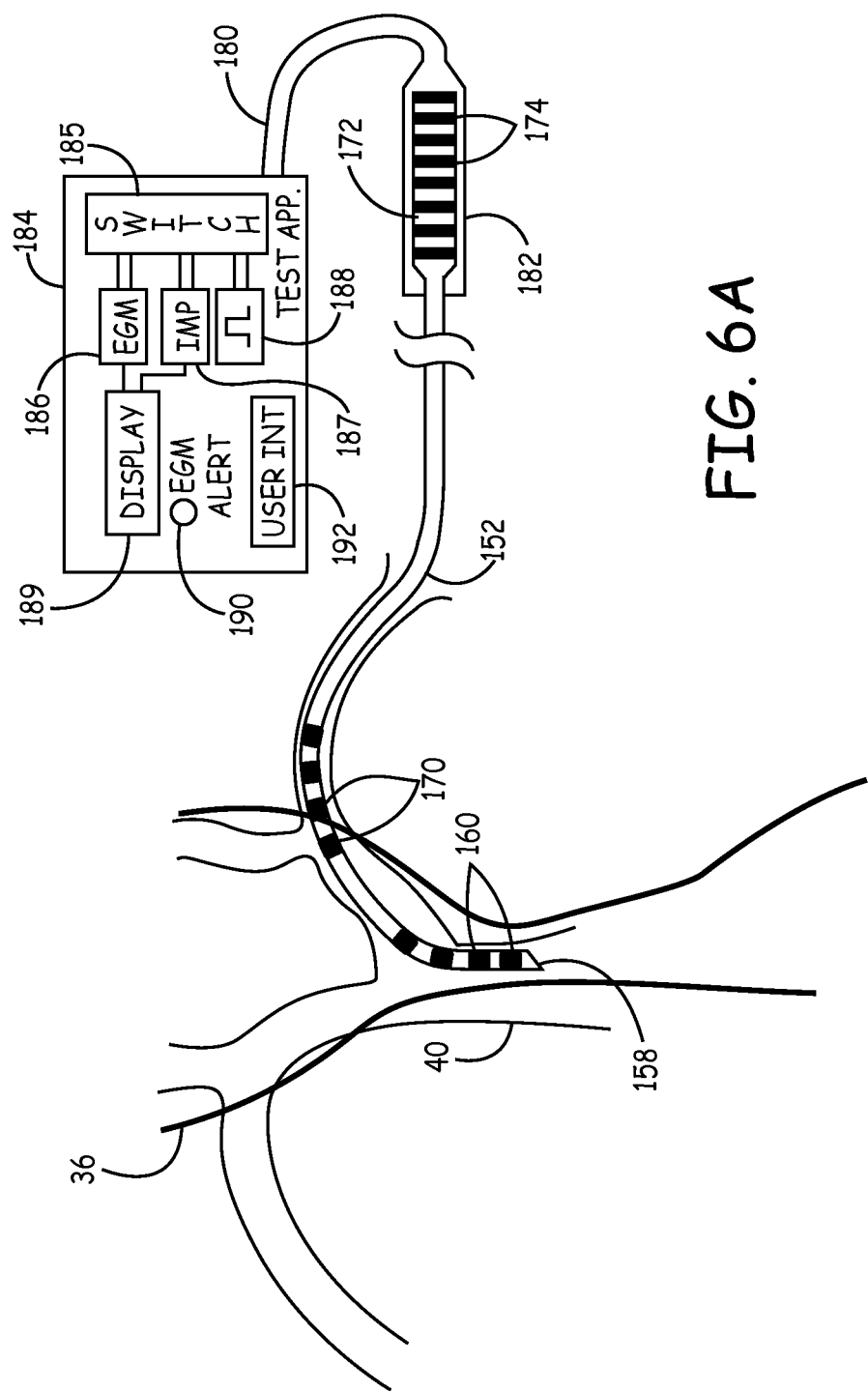
FIGS. 6A and 6B are schematic diagrams of an implantation procedure for positioning an IMD system for phrenic nerve stimulation.
Figure 6B:
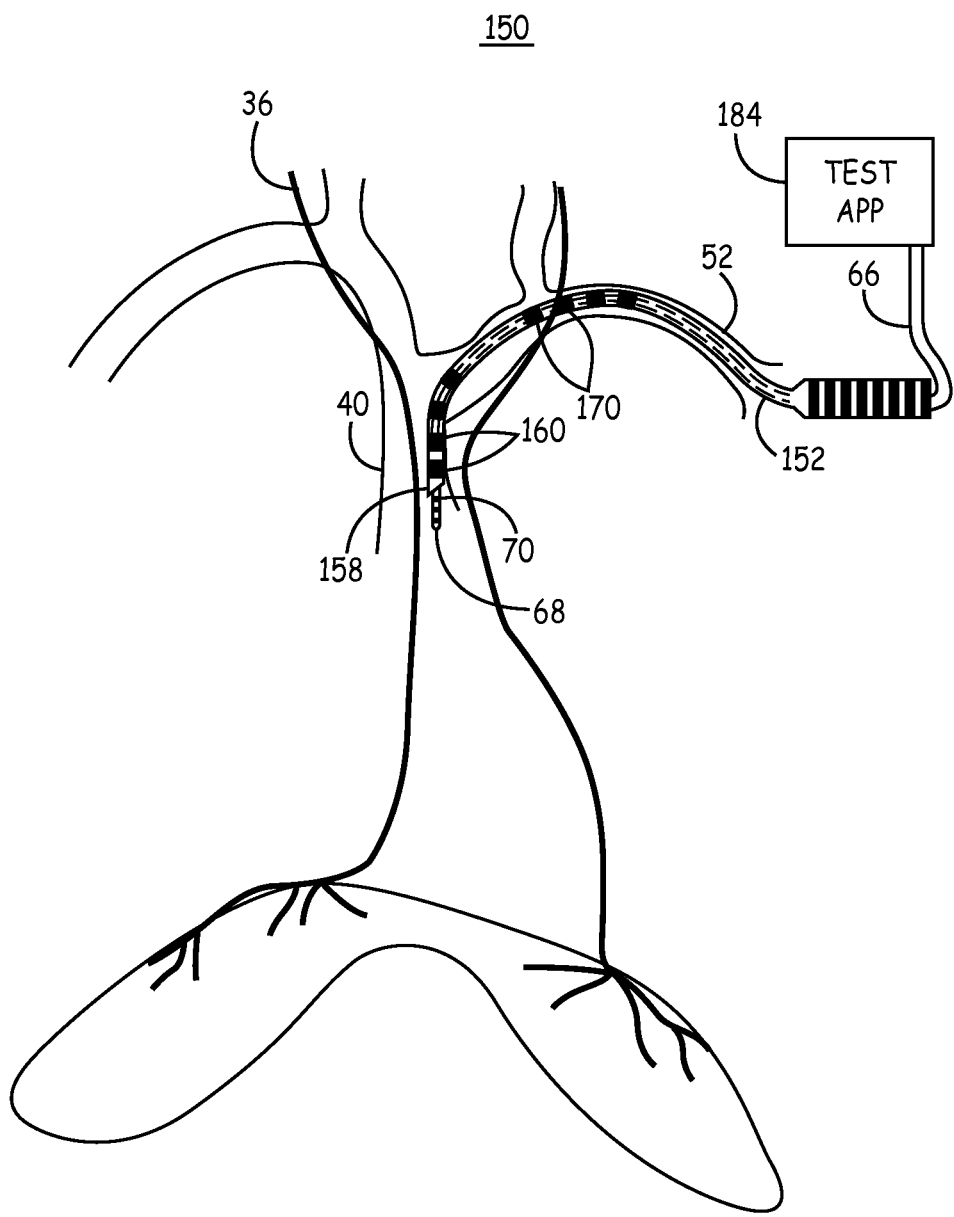

FIGS. 6A and 6B are schematic diagrams of an implantation procedure for positioning an IMD system for phrenic nerve stimulation. In FIG. 6A, a delivery and mapping catheter 152 is advanced to position a distal catheter end 158 in the SVC 40. Catheter 152 is provided with multiple distal electrodes 160 (four shown in FIG. 6A) and multiple proximal electrodes 170 (four shown). The multiple distal and proximal electrodes 160 and 170 may correspond to the electrode configuration of a chronically implantable phrenic nerve stimulation lead. Alternatively, catheter 152 may be provided only with distal electrodes 160 since the distal portion of catheter 152 (and a subsequently implanted lead) is the most likely portion to fall within or near enough to the patient's heart to result in inadvertent cardiac capture.

Catheter 152 includes a proximal connector assembly 172 including connectors 174 that enable either direct connection to a test apparatus 184, or cable 180. A cable may be provided with a female connector portion 182 for receiving connector assembly 172. Alternatively, catheter 152 may be configured for direct coupling to an IMD 10. Test apparatus 184 may be provided as an external testing apparatus used in conjunction with the delivery and mapping catheter 152 during the implantation procedure for identifying a desired lead implant site before a chronically implantable phrenic nerve stimulation lead and associated IMD are implanted. It is recognized that in other embodiments the phrenic nerve stimulation lead may be implanted and tested directly for identifying a desired implant site without the use of electrodes on a delivery catheter. The nerve stimulation lead may be coupled to the test apparatus 184 as shown here or directly to the IMD during implant procedure testing.

Test apparatus 184 may include automatic switching circuitry 185 that selectively couples distal electrodes 160 and optionally the proximal electrodes 170 to EGM sensing circuitry 186 for monitoring for the presence of an EGM signal on any of the electrodes 160 and 170. In one embodiment, only the distal most pair of electrodes 160, nearest distal end 158, is coupled to EGM sensing circuitry during advancement of catheter 152 for detecting an EGM signal. If an EGM signal is detected automatically by EGM detection circuitry 186, an EGM alert 190, which may include an LED and/or audible sound, may be activated to notify a clinician. The EGM signal may be displayed on display 189 for verification of the presence of an EGM signal by the clinician.

If stimulation of the right phrenic nerve is to be delivered from a SVC location, verification of no EGM sensing or no capture of the heart or cardiac nerves along all or at least some of electrodes 160, may be performed. Once verified, activation of the right phrenic nerve may be verified by delivering stimulation pulses from pulse generator 188 via switching circuitry 185 using various combination of selected electrodes 160 and a default supra-threshold stimulation pulse amplitude.

Any of electrodes 160 and 170 may be used for delivering a drive current and measuring a resulting impedance signal by coupling the drive and measurement electrode pairs to impedance measuring circuitry 187. Examples of thoracic impedance measurement methods that can be used for monitoring a respiration signal are generally described in U.S. Pat. No. 4,901,725 (Nappholz), U.S. Pat. No. 6,076,015 (Hartley), and U.S. Pat. No. 5,824,029 (Weijand, et al), all of which are hereby incorporated herein by reference in their entirety. User commands for selecting electrodes for delivering stimulation, selecting impedance measuring electrodes, and selecting stimulation parameters may be entered via a user interface 192. Alternatively, a programmed test sequence may be performed automatically with impedance measurement results for different test conditions displayed on display 189.

Referring now to FIG. 6B, once an acceptable implant location has been identified, the nerve stimulation lead 66 may be advanced through the delivery catheter 152 until the lead distal end 68 reaches the catheter distal tip 158. Lead distal end 68 is not advanced more distally than the catheter distal tip 158. Catheter 152 is shown partially withdrawn over lead 66 to expose the distal electrodes 70 of lead 66. A proximal connector assembly (not shown) of lead 66 may be coupled to test apparatus 184, or directly to IMD 10, to allow verification of successful capture of right phrenic nerve 36 by distal electrodes 70 with no EGM sensing and/or no change in heart rate during phrenic nerve stimulation. The lead 66 may be disconnected from apparatus 184 or IMD 10 to allow complete withdrawal of catheter 152 from lead 66. Further testing of the most effective electrodes and stimulation parameters may be performed. Lead 66 may then be fixed in place and coupled to IMD 10 for chronic implantation.

In alternative embodiments, testing of a phrenic nerve lead or a corresponding delivery catheter intended for a implantation site along the RIV 42 or junction of the RSV 48 and RJV 46, as generally shown in FIG. 1, may involve monitoring for EGM sensing and/or cardiac capture using a most proximal electrode pair of distal electrodes 20 and a most distal electrode pair of proximal electrodes 22 to verify that none of these electrodes, if selected for delivering nerve stimulation, risk inadvertent cardiac capture or stimulation of cardiac nerves.

It is intended that at least the electrodes in closest proximity to the patient's heart are monitored for the presence of an EGM signal or tested for causing a heart rate change due to phrenic nerve stimulation during implantation, and again during therapy delivery as will be described below. Depending on the implant configuration, the electrodes in closest proximity to the heart may be electrodes included in the proximal electrodes 22, 72, 92 and 170 of respective leads 16, 66, 86 and catheter 152 and/or distal electrodes 20, 70, 90, and 160 of respective leads 16, 66, 86, and catheter 152 (FIGS. 1-3 and FIG. 6A). It is further recognized that the electrodes in closest proximity to the heart (or a cardiac nerve) may change during advancement of the lead or catheter to a desired location. Accordingly, the electrodes being monitored for the presence of an EGM signal or tested for capturing the heart or a cardiac nerve may be changed based on the location of the electrodes relative to the heart or cardiac nerves.

For example, as the lead 16 shown in FIG. 1 is advanced to the right innominate vein, initially a distal most electrode pair out of distal electrodes 20 may be monitored for EGM sensing. As the lead is advanced further, a more proximal pair of electrodes 20 may be monitored for EGM sensing. As the lead is advanced even further, a distal pair of proximal electrodes 22 may be monitored for EGM sensing. Once positioned at a desired implant site, the most proximal of the distal electrodes 20 and the most distal of the proximal electrodes 22 may be monitored to detect the presence of an EGM signal and/or cardiac capture due to dislodgement of the lead 16 toward or into the patient's heart.

Figure 7:
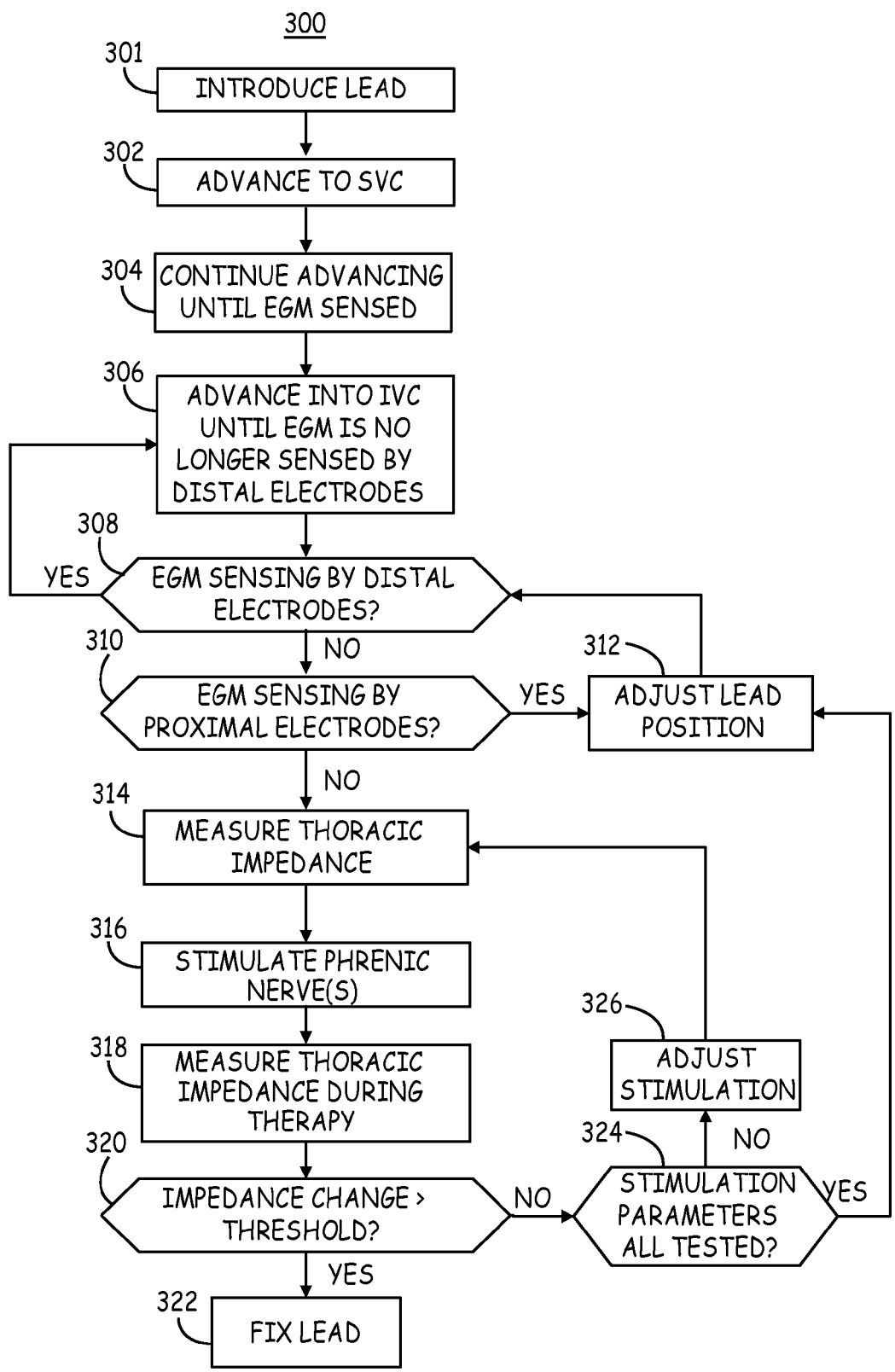
FIG. 7 is a flow chart of a method for implanting a phrenic nerve stimulation lead according to another embodiment.

FIG. 7 is a flow chart 300 of a method for implanting a phrenic nerve stimulation lead according to another embodiment. The method shown by flow chart 300 will be described with reference to lead 86 of FIG. 3, with a targeted implant location of the distal lead end 88 in the IVC near the level of the diaphragm. At block 301, a phrenic nerve stimulation lead, (or a delivery catheter having electrodes spaced apart at locations corresponding to electrode locations on the lead) is introduced through a venous access site. The lead (or catheter) is advanced to the SVC at block 302.

During continued advancement of the lead (or catheter), optionally with the use of fluoroscopy or other imaging, the most distal electrode pair is monitored to detect an EGM signal at block 304. Once the EGM signal is sensed indicating that the distal lead or catheter end is in the RA, the lead (or catheter) is advanced further at block 306 until the EGM is no longer sensed, indicating the distal end has been advanced out of the RA into the IVC.

Additionally at block 306, the EGM signal monitoring may be switched from a most distal pair of distal electrodes 90 to a most proximal pair of the distal electrodes 90. Once the distal end 88 of lead 86 is located in the IVC, some distal electrodes 90 may remain near the heart depending on the number and spacing of the electrodes. As such, it may be desirable to advance lead 86 further distally until the most proximal electrode pair of distal electrodes 90 can no longer sense an EGM signal.

Once an EGM signal is no longer sensed by distal electrodes 90, or at least by a most distal pair of electrodes to enable safe right phrenic nerve stimulation with minimized risk of inadvertent cardiac capture, EGM signal monitoring may be performed at block 310 to determine if an EGM signal can be sensed using any of proximal electrodes 92. In one embodiment, the most distal pair of proximal electrodes 92 is tested for EGM sensing. If the most distal pair does not sense an EGM signal, proximal electrodes 92 are most likely far enough from the heart to avoid inadvertent cardiac capture. In another embodiment, a most proximal pair of electrodes 92 is tested. If at least one proximal pair of electrodes 92 does not sense an EGM signal, that pair can be selected for stimulation of the left phrenic nerve.

If EGM sensing by any (or selected ones) of proximal electrodes 92 is present, the lead position is adjusted at block 312. Lead adjustment typically involves retraction of the lead to a more proximal location to move proximal electrodes 92 further from the heart. In this case, EGM sensing by distal electrodes may be retested at block 308 to ensure that the distal electrodes have not been moved to a location that is associated with a risk of cardiac capture. In one embodiment, only the most proximal pair of distal electrodes 90 is monitored to determine if an EGM signal can be sensed. If no EGM sensing is present on the most proximal pair of the distal electrodes, all of distal electrodes 90 may be presumed to be far enough from the patient heart to avoid cardiac capture. In another embodiment, the most distal electrode pair of electrodes 90 is tested. If at least the most distal pair does not sense an EGM signal, that most distal pair can be selected for right phrenic nerve stimulation.

In other embodiments, testing for capture of the heart or cardiac nerves by monitoring a heart rate using any available cardiac EGM or ECG signals may be performed in addition to, or alternatively to, monitoring for EGM sensing at blocks 308 and 310, during delivery of stimulation pulses using any of the distal electrodes 90 and/or proximal electrodes 92.

After at least one pair of proximal electrodes 92 and at least one pair of distal electrodes 90 are verified as not sensing an EGM signal or causing undesired cardiac capture, pre-stimulation thoracic impedance measurements are acquired at block 314 as previously described in conjunction with FIG. 5. One or both phrenic nerves may then be stimulated at block 316, e.g. using default supra-threshold stimulation parameters and a pair of electrodes verified to not be sensing an EGM signal or at least not capturing the heart or cardiac nerves.

The thoracic impedance measurement(s) are repeated at block 318 during stimulation (which may include measurements performed during and/or between pulse trains) to determine if an impedance measurement change due to stimulation meets some minimum expected threshold of improvement (block 320). If a threshold level of improvement is not reached, other stimulation parameters may be tested by adjusting the stimulation at block 326, using only electrodes known not to be sensing an EGM signal or causing a change in heart rate.

If a maximum number of attempts to improve the impedance measurement by stimulation parameter adjustment is reached, as determined at block 324, the lead position may need to be readjusted at block 312. In this case, and in other methods described herein where lead adjustment is performed, lead adjustment may include placing a new lead or leads having different dimensions and electrode configuration which may provide a better fit to the anatomy of an individual patient for successful transvenous phrenic nerve stimulation.

If the lead position is readjusted or a new lead is placed, the process returns to block 308. Testing for the presence of an EGM signal (and/or cardiac capture) using any of the distal electrodes 90 continues until the absence of an EGM signal and/or cardiac capture using at least selected ones of the proximal and distal electrodes 92 and 90 is verified and an acceptable improvement in the impedance measurement(s) is achieved.

Once an acceptable implantation site is identified based on the EGM and impedance signal testing, the lead may be fixed and coupled to IMD 10 to enable therapy delivery (block 322). If the testing described in conjunction with flow chart 300 is performed using a delivery and mapping catheter, the lead is advanced through the catheter, the catheter is withdrawn, and final verification of lead performance (i.e. absence of EGM sensing or cardiac capture using selected electrodes and adequate impedance measurement improvement) is performed and the lead is fixed in place.

Figure 8:
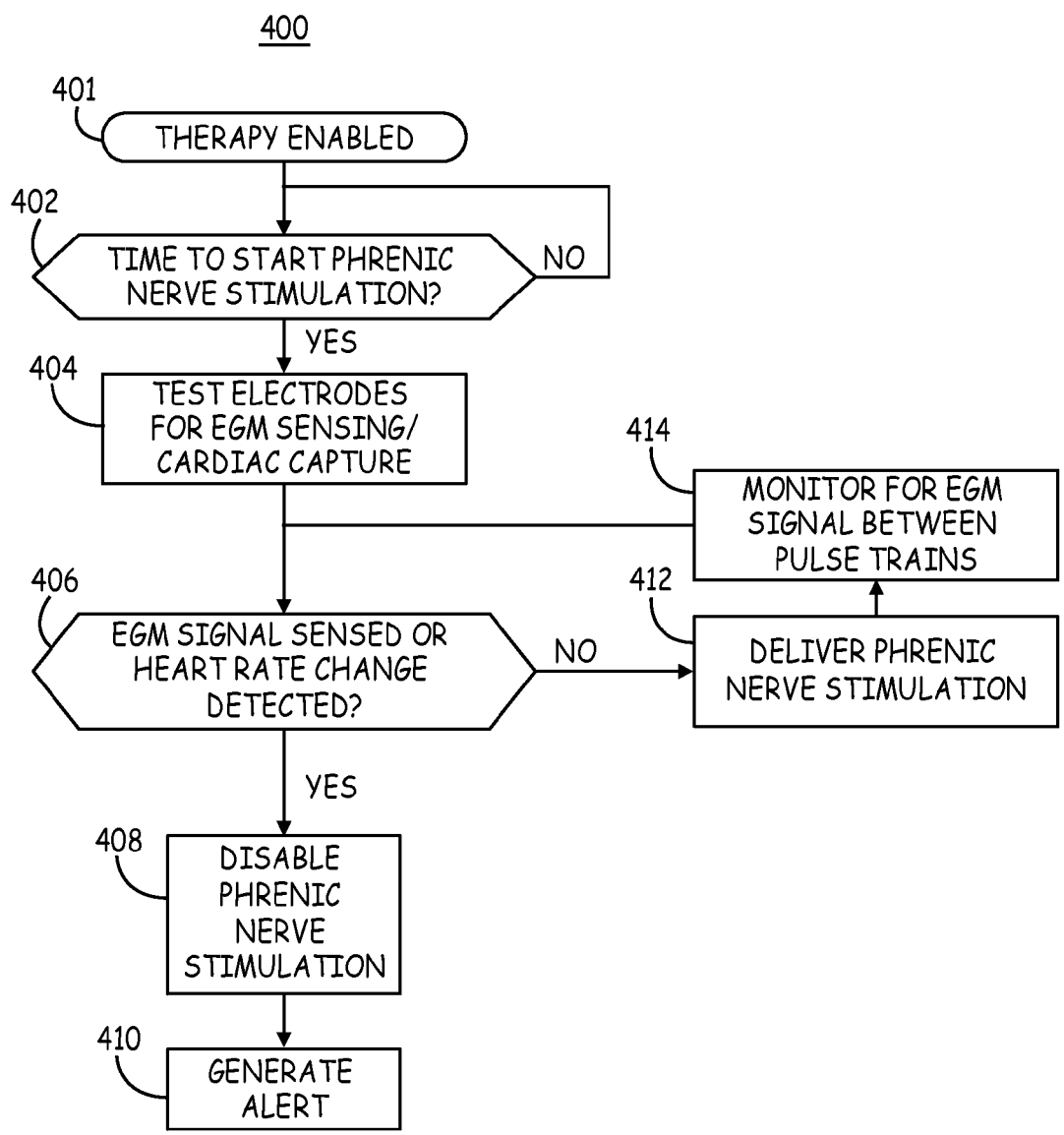
FIG. 8 is a flow chart of a method for delivering stimulation of the phrenic nerve stimulation therapy according to one embodiment.

FIG. 8 is a flow chart 900 of a method for delivering a phrenic nerve stimulation therapy according to one or more embodiments. At block 401, phrenic nerve stimulation therapy is enabled. The nerve stimulation lead is positioned at a desired implant location using any of the methods described above, coupled to IMD 10, and the therapy is enabled according to a desired stimulation protocol for a given patient.

At block 402, a determination is made whether it is time to start phrenic nerve stimulation. In some embodiments, phrenic nerve stimulation is started immediately upon enabling the therapy. In other embodiments, stimulation may be scheduled to occur on a periodic basis, started upon a user command or user activation, or started in response to a change in another physiological signal monitored by the IMD.

If it is time to start phrenic nerve stimulation, the electrodes that are to be used for delivering stimulation pulses, which may be for right, left or both right and left nerve stimulation, are tested for EGM sensing and/or cardiac capture at block 404. Otherwise, the process continues to wait until it is time to start nerve stimulation as determined at block 402.

Testing of electrodes for EGM sensing at block 404 may involve selecting a test electrode pair via switching circuitry to couple the test pair to EGM sensing circuitry. The EGM sensing circuitry output is analyzed for regular sensed cardiac events and/or EGM morphology analysis is performed. One or more electrode pairs may be tested. Only the electrode pair that is known to be closest to the patient's heart and selected for use for delivering nerve stimulation may be tested. For example, if right phrenic nerve stimulation is being achieved by electrodes positioned in the SVC (e.g. as in FIG. 2), only the electrode pair selected from the distal electrodes for right nerve stimulation is tested for EGM sensing. Any other more proximal electrodes and electrodes not selected for delivering stimulation pulses are not tested.

Testing at block 404 may additionally or alternatively include delivering single pulses, maximum pulse energy pulses, or other test stimulation pulses to selected test electrodes and monitoring for a change in heart rate as generally described above.

In some embodiments, electrodes known to be closest to the heart and electrodes to be used for stimulation are tested at block 404. Multiple electrode pairs may be tested for EGM sensing and/or cardiac capture in an automated, sequential or simultaneous manner using a multi-channel EGM sensing circuit.

If an EGM signal is sensed or a heart rate change during phrenic nerve stimulation is detected, as determined at block 406, phrenic nerve stimulation may be disabled at block 408.

In other embodiments, if EGM sensing is present, as long as no cardiac capture is detected, phrenic nerve stimulation may still be delivered by advancing to block 412. If a change in heart rate due to inadvertent capture of the heart or a cardiac nerve during phrenic nerve stimulation is detected, phrenic nerve stimulation is disabled at block 408.

A patient alert signal may be generated at block 410 in response to disabling phrenic nerve stimulation. EGM sensing and/or cardiac capture by an electrode pair of the phrenic nerve stimulation lead indicates possible lead dislodgement, risk of inadvertent cardiac stimulation, and reduced effectiveness of phrenic nerve stimulation. An alert generated at block 410 notifies the patient or clinician that the lead position needs to be re-evaluated before phrenic nerve stimulation resumes. Phrenic nerve stimulation therapy may require manual re-enabling after being disabled due to EGM sensing.

In an alternative embodiment, if one electrode pair that is selected for nerve stimulation can sense an EGM signal or captures the heart or a cardiac nerve, other electrode pairs may be tested until one is found that does not capture the heart or a cardiac nerve. That pair may be used for nerve stimulation. Various factors will determine whether nerve stimulation therapy continues when one or more electrode pairs are found to sense an EGM signal and/or cause cardiac capture. Such factors include the patient's dependence on phrenic nerve stimulation for respiration, whether the patient has an implantable cardioverter defibrillator, and the relative distance of other electrodes available for nerve stimulation from electrodes sensing an EGM signal or causing a change in heart rate.

If no EGM sensing and/or heat rate change indicating capture of the heart or a cardiac nerve is detected at block 406, phrenic nerve stimulation is delivered as scheduled at block 412. Monitoring for an EGM signal and/or heart rate changes during nerve stimulation may be performed at block 414. Switching circuitry or the use of blanking periods during stimulation pulse delivery may be used to allow for EGM sensing on electrodes used for nerve stimulation in between phrenic nerve stimulation pulse train delivery. Switching circuitry may be used to switch between coupling an electrode pair to EGM sensing circuitry and coupling an electrode pair to a pulse generator. Alternatively, a stimulation pair of electrodes may remain coupled to both a pulse generator and EGM sensing circuitry with blanking periods applied to the EGM sense amplifier during pulse train delivery.

If EGM sensing begins to occur or a change in heart rate is detected during therapy delivery (as determined at block 406), the nerve stimulation therapy may be disabled at block 408. If EGM signals are sensed, further testing checking for heart rate changes or R-wave morphology changes, to verify no capture of the heart or cardiac nerves is occurring may be performed using the same or other electrodes. If no evidence of cardiac capture is found, phrenic nerve stimulation may continue despite EGM sensing.

Figure 9:
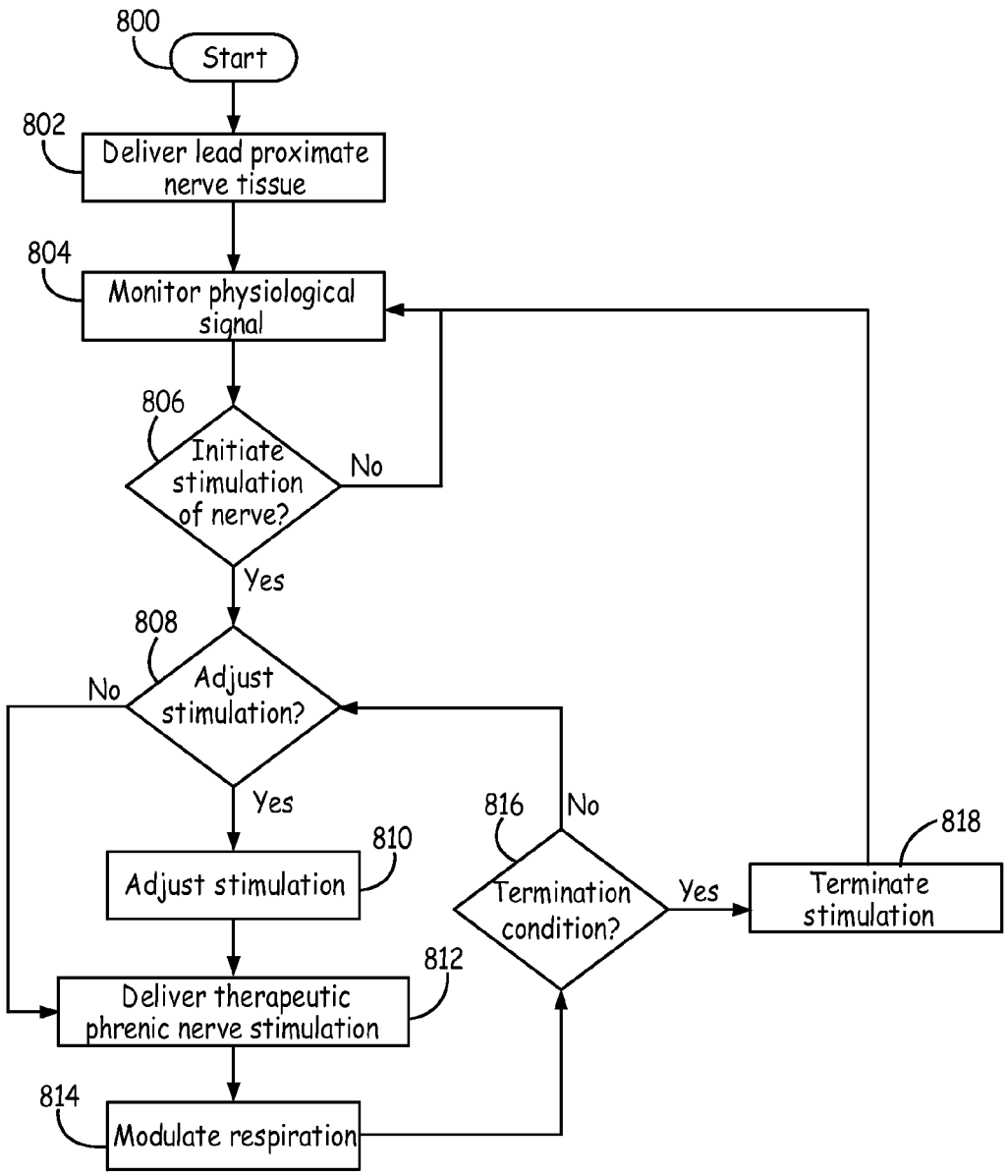
FIG. 9 is a flow chart of a method for initiating, delivering and terminating stimulation of the phrenic nerve stimulation therapy according to one embodiment.

FIG. 9 is a flow chart for controlling respiration through phrenic nerve stimulation such that respiration depth and/or respiration rate are substantially increased. Respiration involves inspiration and expiration in order to exchange oxygen for carbon dioxide. Inspiration involves air flowing past airways into the lungs and the alveoli of the lungs. Inspiration begins with contraction of the diaphragm, which, in turn, increases the negative pressure of the intrapleural space of the lung. Increasing negative pressure in the intrapleural space creates a pressure difference between the atmosphere and alveolus that causes air to flow into the lungs.

Expiration is the opposite of inspiration. Expiration involves moving or expelling carbon dioxide and/or air out of the bronchial tubes, through the airways, to the external environment. Typically, expiration is a passive process that involves recoil of the diaphragm. Recoil of the diaphragm expels air from the lungs until pressure between the atmosphere and in the lungs reaches equilibrium. The abdominal and intercostal muscles can also generate abdominal and thoracic pressure to force carbon dioxide and air out of the lungs.

An exemplary process for phrenic nerve stimulation, presented in FIG. 9, begins at start block 800. At block 802, a medical electrical lead is delivered to, or delivered proximate to, the left and/or right phrenic nerves. The medical electrical lead can be any suitable lead that includes at least one or more electrodes for sensing data and also stimulating the phrenic nerve. Exemplary leads can be those which are described or incorporated herein. Preferably, the lead is placed transvenously. Skilled artisans appreciate that the lead can also be placed transvascularly. Placement of the lead can occur using the technique described herein or other suitable methods for placement of a lead near a nerve.

After the lead has been properly placed proximate the phrenic nerve(s), physiological signals are continuously monitored at block 804. Physiological data is sensed through electrodes and passed to the microprocessor in the implantable medical device. Typically, computer instructions such as firmware continuously monitor physiological signals and store data in the memory of the IMD. Sensing data through the lead and storing that data in the memory can be performed independently of the computer instructions or as part of the computer instructions for FIG. 9.

At block 806, a determination is made as to whether to deliver phrenic nerve stimulation. The IMD can be configured to compare a patient's real time sensed physiological data against one or more predetermined conditions. Predetermined conditions can be set by a physician that are customized for a particular patient or the conditions may relate to a population of patients. Exemplary conditions for initiating electrical stimulation of the phrenic nerve includes a mean blood pressure >120 mmHg, a high resting heart rate (e.g. HR>90 b/min), a $SaO_2$ that is <90%, a glomerular filtration rate (GFR)<30 mL/min/1.73 $m^2$, arterial pH<7.35, and/or baroreflex gain<6 ms/mmHg. Preferably, the arterial pH condition is used to activate the phrenic nerve stimulation. Arterial pH is believed to provide reliable and possibly more relevant data than the other stated conditions. Typical pH of arterial blood generally lies between 7.35 and 7.45. However, it is generally understood that patients experiencing heart failure may have an arterial blood pH that exceeds the normal range. In one or more embodiments, it may be desirable to seek to gradually improve a heart failure (HF) patient's physiological response. Therefore, use of arterial blood pH to terminate electrical stimulation of the phrenic nerve may be specified by a physician. For example, if a HF patient had a typical arterial blood pH that ranged from 7.30 to 7.40, then the physician would require that electrical stimulation to the phrenic nerve activate and/or terminates once arterial blood pH is determined to be within the typical range for that particular patient. Customizing activation and/or termination of electrical stimulation to the phrenic nerve(s) based on a patient's physiological condition can assist the patient in optimizing his or her physiological response to the therapy. Arterial pH can be determined through an ion device as found in US Patent Pregrant Publication No. 2007-0138027 A1 filed on Dec. 15, 2005, U.S. Pat. No. 4,519,973 issued May 28, 1985, the disclosures of which are incorporated by reference in their entirety. The lead for detecting arterial pH can be placed in an artery (e.g. artery in an arm or leg etc.). Arterial blood saturation level of oxygen ($SaO_2$ in hemoglobin is another preferable predetermined condition that is very useful for determining when to initiate phrenic nerve stimulation.

In one or more other embodiments, phrenic nerve stimulation can be continuously activated by the physician implanting the IMD 10; therefore, it is unnecessary to detect and/or determine the presence of a stimulation condition. Continuously activated phrenic nerve stimulation may be used in cases where the patient is unable to breathe on his own.

One or more other embodiments rely on the detection and/or determination of the presence of a stimulation condition. If a stimulation condition is not met by the data from the patient, the method can be continued by following the NO return path to monitoring the physiological signals at block 804. If one or more of predetermined stimulation condition(s) is met, the method can be continued by following the YES path to block 808 that involves an optional step of adjusting (i.e. increase or decrease values) stimulation parameters values. Stimulation parameters associated with delivering electrical stimulation through the lead to phrenic nerve tissue can include at least one or more of current amplitude, voltage, frequency, and/or pulse width. In one or more embodiments, current amplitude can be in the range of about 2 to about 20 mA. Voltage can be in the range of about 1 volt to about 8 volts. Frequency can be in the range of about 20 to 100 Hz. Pulse width can be in the range of about 20 to 400 microseconds ($\mu s$). At block 810, one or more stimulation parameters are adjusted to meet stimulation protocols stored in memory.

If no adjustment is necessary, the method can be continued by following the NO path to block 812 where therapeutic phrenic nerve stimulation is delivered through one or more electrodes on a lead. Adjustment may be needed if the initiation conditions are persistent and alternative therapy protocols to reach to a termination conditions exist. If stimulation adjustment is necessary, the method can be continued by following the YES path to block 812 where therapeutic phrenic nerve stimulation is delivered through one or more electrodes on the lead in accordance with predetermined protocols. The protocols indicate one or more stimulation parameters for delivery of electrical stimulation to the phrenic nerve tissue. Protocols are stored in memory and accessed by the microprocessor of the implantable medical device.

In one or more embodiments, delivery of electrical stimulation to phrenic nerve tissue can be performed without the need to sense inspiration or expiration cycles. In this embodiment, electrical stimulation such as pulses can be delivered after a fixed delay. Delivery of electrical stimulation without sensing and processing inspiration or expiration cycles can save on computational cycles which can preserve battery capacity of the implantable medical device.

After pulses of electrical stimulation have been delivered to the phrenic nerve, involuntary or voluntary modulated respiration begins to occur at block 814. Modulating respiration can drive or override intrinsic respiration.

In one or more embodiments, modulated respiration exhibits substantially deep respiration. Deep respiration can be similar to the type of breathing taught in a yoga class. For example, deep respiration can be a substantial increase in tidal volume compared to tidal volume measure before phrenic nerve tissue stimulation. Tidal volume is a normal volume of air displaced between normal inspiration and expiration in a patient. In a healthy individual tidal volume values are around 500 ml or 7 ml/kg of bodyweight. Tidal volume can be measured by a spirometer or other suitable instrument. Tidal volume is the volume of gas inhaled and exhaled during one respiratory cycle. Respiratory cycle includes an inspiration cycle and an expiration cycle. Inspiration cycle is initiated by the delivery of the therapy during which the diaphragmatic muscles are contracting thereby increasing the volume of the thoracic cavity and inhaling air into the lungs. The expiration cycles starts immediately after the cessation of the delivery of the electrical therapy and during which the diaphragmatic muscles relax passively and thereby decrease the volume of the thoracic cavity and expelling air from the lungs. In one or more embodiments, a patient's tidal volume is increased by up to or at least 10% compared to a patient's tidal volume before initiation of phrenic nerve stimulation. In one or more other embodiments, a patient's tidal volume is increased by up to or at least 15% compared to a patient's tidal volume before initiation of phrenic nerve stimulation.

Assuming inspiration is constant, respiration can be expressed as follows:

$$\text{Respiration }(t)=\text{Tidal Volume}$$

By implementing techniques described herein, tidal volume can be expressed as follows:

$$\text{Tidal Volume }(t)=\text{Baseline Tidal volume}*(1+A*\cos(w*t))$$

Such that A is the breath by breath modulation amplitude (i.e. about 10 to 15% of baseline tidal volume). W is the modulation frequency which is less than the respiration frequency of around 0.05 to 0.3 Hertz (Hz)).

In one or more other embodiments, the modulated respiration exhibits a decreased respiration rate. The respiration rate is defined as the half the number of combined inspiration and expiration cycles per minute. Decreased respiration rate is shown by comparing the decreased respiration rate while undergoing stimulation of the phrenic nerve(s) to that of the respiration rate of the patient without phrenic nerve stimulation. The decreased respiration rate allows increased tidal volumes by maintaining or exceeding the volume of air respired within a minute.

In one or more embodiments, modulating respiration asynchronously modifies any intrinsic respiration. Asynchronous means that the modulating respiration may not be occurring at the same time as intrinsic respiration. Intrinsic respiration is respiration that occurs based solely upon the patient's ability for inspiration and/or expiration without the use of a device to assist in breathing. In one or more embodiments, the modulating respiration occurs without any intrinsic respiration being present which occurs when a patient is paralyzed or experiencing a respiratory condition such as high spinal cord injuries, congenital central hypoventilation syndrome, central alveolar hypoventilation (due to strokes, tumors, malignancy, trauma and surgery), central sleep apnea and the like.

At block 816, a determination is made as to whether a termination condition is detected so that phrenic nerve stimulation can be automatically or manually terminated. Termination conditions are determined to exist, either through a physician and/or IMD 10 implementing known diagnostic analyses. In one or more other embodiments, the stimulation parameters can be adjusted (i.e. decreased or increased) in a manner that eliminates the presence of a termination condition.

Predetermined termination conditions may be one or more conditions related to protection conditions, efficacy conditions, comfort conditions, and/or prescription conditions. Protection conditions may be able to prevent an undesired effect or condition from occurring due to phrenic nerve tissue simulation. For example, it is desirable to avoid inadvertent capture of heart or skeletal muscle. Inadvertent capture of a heart or skeletal muscle can be detected through far field EGM techniques when implanting the IMD 10. Post-implant EGMs can also be viewed to determine if inadvertent capture of heart or skeletal muscle is occurring. Inadvertent capture of a heart or skeletal muscle can allow the stimulation parameters (or pacing energy) to be terminated.

Diaphragmatic fatigue can also be detected through an EGM. Alternatively, a patient may notice a diaphragmatic twitch or hiccup which may be indicative of diaphragmatic fatigue. Once it is determined diaphragmatic fatigue is present, electrical stimulation of the phrenic nerve can be terminated.

Yet another protection condition can be carbon dioxide ($CO_2$) in the blood. During hyperventilation, which could occur if the tidal volume and respiration rate are too large, the $CO_2$ tension in the blood would be lower than a prescribed lower range for a patient.

Efficacy conditions target ranges for arterial blood pressure, heart rate and/or deviation from a predetermined range of pH of arterial blood saturation level of oxygen ($SaO_2$) in hemoglobin. One or more of efficacy conditions require that IMD 10 detect whether the patient is exhibiting health efficacy conditions. Once the patient is within a healthy range for one or more efficacy conditions, IMD 10 can terminate the phrenic nerve stimulation.

Comfort conditions are another type of condition that can be used to terminate phrenic nerve stimulation. Exemplary comfort conditions can relate to a patient's mobility as detected by an activity sensor, vocalized responses from a patient as detected by a microphone, and/or a patient manually terminating phrenic nerve stimulation.

Prescriptive conditions are still yet another type of condition that can be used to terminate phrenic nerve stimulation. Exemplary prescriptive conditions include a predetermined number of programmed breaths, an optional breathing pattern, a predetermined duration for stimulation or termination activated by the patient. $SaO_2$ is a measure of the amount of oxygen in the blood. Low levels of $SaO_2$ can be indicative of impaired respiration. $CO_2$ tension measures relative concentration of $CO_2$ in expired air. Higher levels of $CO_2$ can occur during low cardiac output or impaired respiration.

If the termination condition is detected, the YES path terminates stimulation at block 818 and the process returns to monitoring physiological signals at block 804. If no termination condition is detected, then the NO path determines whether stimulation needs to be adjusted at block 808. As shown, FIG. 9 is a closed loop therapy method that seeks to continuously achieve deep inspiration and deep expiration breathing, similar to yoga breathing. In other words, consistently and repeatedly performing deep inspiration and deep expiration breathing can be automatically implemented for extended time periods. Extended periods of time can be 24 hour period. Other time periods can be at least 15 minutes or more. The present disclosure allows achieves modulating respiration without thinking about the process which can be required when doing yoga breathing.

It is believed that consistently modulating respiration to obtain modulating respiration of deep inspiration and deep expiration can improve a patient's cardiorenal health. Improvement of cardiorenal health is believed to be based upon, for example, the modulating respiration can activate stretch receptors that are found in the heart, in the great veins and in the lungs. Activating or effecting the stretch receptors may influence or affect the vagal nerve (afferent and/or efferent tissue) and/or sympathetic nervous system in the brain. Through modulation of the respiration the amplitude of this spillover effect could be controlled.

Additionally, GFR, the flow rate of fluid filtered through a kidney, can be improved. It is believed GFR can improve by at least 5-10% compared to a patient's GFR prior to initiation of phrenic nerve stimulation. Also, cardiac afterload can be reduced through the modulating respiration. Moreover, blood acid-base balance is improved. Accordingly, patients experiencing HF, kidney failure or hypertension may be able to benefit from the methods disclosed herein. The present disclosure automatically controls respiration, which in turn enhances renal function. Thus, a method and apparatus for providing phrenic nerve stimulation therapy have been presented in the foregoing description with reference to specific embodiments. It is appreciated that various modifications to the referenced embodiments may be made without departing from the scope of the disclosure as set forth in the following claims.

The invention claimed is:

1. A method of controlling respiration depth or respiration rate through an implanted medical electrical lead having an electrode for pacing and sensing, the method comprising:
    delivering electrical stimulation through an electrode proximate phrenic nerve tissue, and
    eliciting modulating respiration in response to electrical stimulation of the phrenic nerve, the modulating respiration asynchronously modifies intrinsic respiration,
    wherein glomerular filtration rate (GFR) is improved by about 10% compared to another GFR before any phrenic nerve stimulation has occurred.

2. The method of claim 1 wherein the modulating respiration overrides any intrinsic respiration.

3. The method of claim 1 wherein the electrical stimulation includes at least one stimulation parameter including one of current amplitude, voltage, frequency, and pulse width.

4. The method of claim 3 wherein the current amplitude is in the range of about 2 to about 20 milliampere (mA).

5. The method of claim 3 wherein the voltage is in the range of about 1 volts to about 8 volts.

6. The method of claim 3 wherein the frequency is in the range of about 20 to about 100 Hertz (Hz).

7. The method of claim 3 wherein the pulse width is in the range of about 20 to about 400 microseconds ($\mu s$).

8. The method of claim 2 wherein modulation respiration occurs involuntarily.

9. The method of claim 2, wherein a modulated strength of respiration is adjusted by about 10% of a total tidal volume as compared to total tidal volume before initiation of phrenic nerve stimulation.

10. The method of claim 2, wherein a modulated strength of respiration is adjusted by about 15% of a total tidal volume as determined before any phrenic nerve stimulation occurs in a patient.

11. The method of claim 1 wherein phrenic nerve stimulation is through transvenous phrenic nerve stimulation.

12. The method of claim 1 further comprising terminating phrenic nerve stimulation in response to detecting a predetermined terminating condition.

13. The method of claim 12 wherein the predetermined terminating condition is a cardiovascular physiological condition.

14. The method of claim 12 wherein the cardiovascular physiological condition is one of mean arterial blood pressure, and heart rate.

15. The method of claim 14 wherein the mean arterial blood pressure having a range of about 70 mmHg and about 110 mmHg.

16. The method of claim 14 wherein the heart rate having a range of about 40 beats per minute (BPM) and about 80 BPM.

17. The method of claim 12 wherein the predetermined terminating condition is saturation level of oxygen ($SaO_2$) in hemoglobin, wherein the $SaO_2$ is in the range of about 92% to about 100%.

18. The method of claim 12 wherein the predetermined condition is inadvertent capture of one of a heart and skeletal muscle.

19. The method of claim 12 wherein the predetermined condition is diaphragmatic fatigue.

20. The method of claim 12 wherein the predetermined condition is carbon dioxide ($CO_2$) tension in blood.

21. The method of claim 12 wherein the predetermined condition is one of a predetermined number of programmed breaths following an apnetic event, a breathing pattern, and a predetermined duration of the therapy.

22. The method of claim 12 wherein the predetermined condition is activated by a patient.

23. A method of controlling respiration depth or respiration rate through an implanted medical electrical lead having an electrode for pacing and sensing, the method comprising:
    delivering electrical stimulation through an electrode proximate phrenic nerve tissue, and
    eliciting modulating respiration in response to electrical stimulation of the phrenic nerve, the modulating respiration asynchronously modifies intrinsic respiration,
    wherein GFR is improved by about 15% compared to another GFR of before any phrenic nerve stimulation has occurred.

24. The method of claim 1, further comprising:
adjusting substantially a respiration depth during the inspiration.

25. The method of claim 1, further comprising:
adjusting substantially a respiration rate.

26. A stimulator system comprising:
a phrenic nerve tissue electrode and a physiological electrode, spatially separated from one another and all coupled to an implantable pulse generator, the implantable pulse generator comprising:
    delivering electrical stimulation through an electrode proximate phrenic nerve tissue, the delivery of electrical stimulation is timed without sensed respiration data, wherein glomerular filtration rate (GFR) is improved by about 10% compared to another GFR before any phrenic nerve stimulation has occurred.

27. A stimulator system comprising:
a phrenic nerve tissue electrode and a physiological electrode, spatially separated from one another and all coupled to an implantable pulse generator, the implantable pulse generator comprising:
    means for delivering electrical stimulation through an electrode proximate phrenic nerve tissue, and
    means for eliciting modulating respiration in response to electrical stimulation of the phrenic nerve, the modulating respiration asynchronously modifies intrinsic respiration, wherein glomerular filtration rate (GFR) is improved by about 10% compared to another GFR before any phrenic nerve stimulation has occurred.

28. A method of controlling respiration depth or respiration rate through an implanted medical electrical lead having an electrode for pacing and sensing, the method comprising:
    delivering electrical stimulation through an electrode proximate phrenic nerve tissue, the delivery of electrical stimulation is timed without sensed respiration data;
    determining whether a termination condition is detected; and terminating phrenic nerve stimulation in response to detecting the termination condition.

29. A method of controlling respiration depth or respiration rate through an implanted electrical lead having an electrode for pacing and sensing, the method comprising:
- determining whether to initiate stimulation of the phrenic nerve based on a predetermined initiation event;
- in response to determining whether to initiate stimulation, delivering electrical stimulation through an electrode proximate phrenic nerve tissue,
- eliciting modulating respiration in response to electrical stimulation of the phrenic nerve, the modulating respiration asynchronously modifies intrinsic respiration;
- detecting a cardiovascular parameter within a predetermined range; and
- terminating electrical stimulation in response to detecting the cardiovascular parameter within the predetermined range wherein glomerular filtration rate (GFR) is improved by about 10% compared to another GFR before any phrenic nerve stimulation has occurred.

30. The method of claim 29 wherein the initiation event is selected from the group consisting of immediately upon enabling stimulation, on a periodic basis, upon user activation, upon user command, or in response to a change in a physiological parameter.

31. The method of claim 30 wherein the physiological parameter is selected from the group consisting of blood pressure, heart rate, pH of arterial blood, and $SaO_2$.

32. The method of claim 30 wherein the physiological parameter is an arterial blood pressure that exceeds a range of 70 to 110 mmHg.

33. The method of claim 30 wherein the physiological parameter is a resting heart rate which falls outside a range of 40 to 80 beats per minute.

34. The method of claim 30 wherein the physiological parameter is a pH of arterial blood which falls outside a predetermined normal range for a patient.

35. The method of claim 30 wherein the physiological parameter is a pH of arterial blood which falls outside a range of about 7.35 to about 7.45.

36. The method of claim 30 wherein the physiological parameter is a $SaO_2$ which falls outside of a range of about 92% to about 100%.

37. The method of claim 29 wherein terminating stimulation of the phrenic nerve occurs when the pH of arterial blood falls within a predetermined normal range for a patient.

38. The method of claim 29 wherein terminating stimulation of the phrenic nerve occurs when the pH of arterial blood is within the range of about 7.35 to about 7.45.

39. A neurostimulator system comprising:
- a pulse generator;
- a medical electrical lead having one or more electrodes, the medical electrical lead connected to the pulse generator;
- means for stimulating phrenic nerve tissue;
- modulating respiration in response to stimulating phrenic nerve stimulation; and
- means for terminating phrenic nerve stimulation without using respiration data, wherein glomerular filtration rate (GFR) is improved by about 10% compared to another GFR before any phrenic nerve stimulation has occurred.

40. The stimulator system of claim 39 wherein terminating phrenic nerve stimulation is in response to detecting one of pH of arterial blood and $SaO_2$.

41. A method of controlling ventilation depth or ventilation rate through an implanted electrical lead having an electrode for pacing and sensing, the method comprising:
- determining whether to initiate stimulation of the phrenic nerve based on a predetermined initiation event;
- in response to determining whether to initiate stimulation, delivering electrical stimulation through an electrode proximate phrenic nerve tissue,
- eliciting modulating ventilation in response to electrical stimulation of the phrenic nerve, the modulating ventilation asynchronously modifies intrinsic ventilation;
- detecting a cardiovascular parameter within a predetermined range; and terminating electrical stimulation in response to detecting the cardiovascular parameter,
- wherein glomerular filtration rate (GFR) is improved by about 10% compared to another GFR before any phrenic nerve stimulation has occurred.

* * * * *